US010196346B2

(12) United States Patent
Li et al.

(10) Patent No.: US 10,196,346 B2
(45) Date of Patent: Feb. 5, 2019

(54) SUBSTITUTED ACETHYDRAZIDE DERIVATIVE, PREPARATION METHOD AND USE THEREOF

(71) Applicant: Institute of Pharmacology and Toxicology Academy of Military Medical Sciences P.L.A. China, Beijing (CN)

(72) Inventors: Song Li, Beijing (CN); Junhai Xiao, Beijing (CN); Lili Wang, Beijing (CN); Long Long, Beijing (CN); Wei Li, Beijing (CN); Haoming Luo, Beijing (CN); Feifei Li, Beijing (CN); Wu Zhong, Beijing (CN); Zhibing Zheng, Beijing (CN); Yunde Xie, Beijing (CN); Xingzhou Li, Beijing (CN); Xinbo Zhou, Beijing (CN); Xiaokui Wang, Beijing (CN); Ruiyuan Cao, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 15/818,076

(22) Filed: Nov. 20, 2017

(65) Prior Publication Data
US 2018/0134653 A1    May 17, 2018

Related U.S. Application Data

(62) Division of application No. 15/314,884, filed as application No. PCT/CN2015/079370 on May 20, 2015, now abandoned.

(30) Foreign Application Priority Data

May 30, 2014    (CN) .......................... 2014 1 0238255

(51) Int. Cl.
| C07C 251/86 | (2006.01) |
| A61K 31/165 | (2006.01) |
| A61K 31/277 | (2006.01) |
| C07C 255/58 | (2006.01) |
| C07C 249/16 | (2006.01) |
| C07C 253/30 | (2006.01) |

(52) U.S. Cl.
CPC .......... C07C 251/86 (2013.01); A61K 31/165 (2013.01); A61K 31/277 (2013.01); C07C 249/16 (2013.01); C07C 253/30 (2013.01); C07C 255/58 (2013.01)

(58) Field of Classification Search
CPC .................. C07C 251/86; A61K 31/165
See application file for complete search history.

(56) References Cited

U.S. PATENT DOCUMENTS

| 4,239,526 A | 12/1980 | Siemer |
| 2007/0060646 A1 | 3/2007 | Gericke et al. |
| 2011/0003851 A1 | 1/2011 | Zhi et al. |

FOREIGN PATENT DOCUMENTS

| CA | 2 542 106 A1 | 4/2005 |
| CN | 101402587 A | 4/2009 |
| JP | 2006-527199 | 11/2006 |
| JP | 2008-545718 | 12/2008 |
| JP | 2011-513206 | 4/2011 |
| WO | WO 03/078386 A1 | 9/2003 |
| WO | WO 2004/108121 A1 | 12/2004 |
| WO | WO 2005/037773 A1 | 4/2005 |
| WO | WO 2009/155362 A1 | 12/2009 |
| WO | WO 2010/060277 A1 | 6/2010 |

OTHER PUBLICATIONS

Communication pursuant to Article 94(3) EPC for EP 15800371.5, dated Jul. 7, 2018, European Patent Office, Munich, Germany.
International Search Report (ISR) for PCT/CN2015/079370; I.A. fd: May 20, 2015, dated Jun. 23, 2015, State Intellectual Property Office of the P.R China, Beijing, China.
International Preliminary Report on Patentability (IPRP) including the Written Opinion of the International Searching Authority (PCT Rule 44bis) for PCT/CN2015/079370; I.A. fd: May 20, 2015, dated Dec. 6, 2016, by the International Bureau of WIPO, Geneva, Switzerland.

(Continued)

*Primary Examiner* — Golam M Shameem

(74) *Attorney, Agent, or Firm* — Sterne, Kessler, Goldstein & Fox P.L.L.C.

(57) ABSTRACT

The present invention pertains to the field of pharmaceutical chemicals, and relates to a substituted acethydrazide derivative, preparation method and use thereof; preferably, relates to a compound of Formula I or a pharmaceutically acceptable salt thereof. The compound of the present invention or a pharmaceutically acceptable salt thereof can effectively inhibit proline hydroxylase, stabilize HIF-α, particularly HIF-1α, and has potency in the manufacture of a medicament for treatment and/or prophylaxis and/or adjuvant therapy of anemia, acute ischemic reperfusion injury.

11 Claims, No Drawings

(56) References Cited

OTHER PUBLICATIONS

Hao-ming, L. et al., "Design, synthesis and antitumor activity of a novel series of PAC-1 analogues," Chem Res Chin Univ (Oct. 2013) 29(5):906-910, doi: 10.1007/s40242-013-3336-8, Higher Education Press, Beijing, China.
Luo et al. (2013): STN International, HCAPLUS database (Columbus, Ohio), Accession No. 2013:1924859.
Luo et al. (2009): STN International, HCAPLUS database (Columbus, Ohio), Accession No. 2009:439480.
First Office Action and English Translation for CN 201410238255.1, dated Feb. 24, 2017, State Intellectual Proprty Office of the P.R. China, Beijing, China.
Extended European Search Report (EESR) for EP 15800371.5, dated Jul. 11, 2017, Munich, Germany.
Second Office Action and English Translation for CN 201410238255.1, dated Aug. 2, 2017, State Intellectual Proprty Office of the P.R. China, Beijing, China.
Office action for Japanese Patent Application No. 2016-569920, dated Oct. 16, 2018, The Japanese Patent Office, Tokyo, Japan.
Hsu, D.C. et al., "Parallel Synthesis and Biological Evaluation of 837 Analogues of Procaspase-Activating Compound 1 (PAC-1)," ACS Combinatorial Science, 2012, vol. 14, No. 1, p. 44-50.
Yeoh, K.K. et al., "Dual-action inhibitors of HIF prolylhydroxylases that induce binding of a second iron ion," Organic & Biomolecular Chemistry, 2013, vol. 11, No. 5, p. 732-745.

SUBSTITUTED ACETHYDRAZIDE DERIVATIVE, PREPARATION METHOD AND USE THEREOF

TECHNICAL FIELD

The present invention pertains to the field of pharmaceutical chemicals, and relates to a substituted acethydrazide derivative, preparation method and use thereof.

BACKGROUND ART

In 1992, Semenza et al. found a protein capable of specifically binding to hypoxia responsible element of erythropoietin gene, and this protein is named as Hypoxia inducible factor-1 (HIF-1). HIF-1 widely exists in mammalian cells, and mainly regulates angiogenesis, cellular survival and death, as well as pH. HIF-1 is a heterodimer consisting of two subunits (HIF-α and HIF-β) and both of these two subunits are members of alkaline helix-loop-helix transcription factor superfamily, and have PER-AHR/ARNT-SIM (PAS) domain. HIF-α has 3 subunits, which are separately HIF-1α, HIF-2α and HIF-3α, in which HIF-1α and HIF-2α have a high sequence identity, recognize the same DNA binding domain, but have different biological effects.

Under normoxia condition, proline residues at sites 402 and 564 in oxygen-dependent degradation domain (ODDD) of HIF-1α are hydroxylated by prolyl hydroxylase (PHD), and collect ubiquitin proteins such as elongin C, elongin B to form ubiquitin-linking protease complexes and to be degraded via ubiquitin-dependent pathway when they bind to tumor suppressor von Hippel-Lindau gene product (pVHL). Under anoxic conditions, deactivation of PHD results in that proline residues cannot be hydroxylated, HIF-1α cannot bind to pVHL, so that its degradation is hindered.

Activation of HIF-1α results in upregulation of downstream target genes, and this has been confirmed in more than 70 HIF-1α target genes, which widely influence many physiological phenomena such as carcinogenesis, vasculogenesis, cell survival, glucose metabolism, etc. Among the downstream target genes, vascular endothelial growth factor (VEGF) and erythropoietin (EPO) are key growth factors for tumor angiogenesis, glucose transporter (Glut-1) can reduce glucose level, carboanhydrase IX (CAIX) can regulate pH change.

In 2001, Bruick found a protein capable of hydroxylating HIF-α, and then Ivan et al found genes encoding proline hydroxylase in human genes, i.e., EGLN-1, EGLN-2 and EGLN-3, which encode proteins PHD2, PHD1 and PHD3. In 2002, Oehme found the 4$^{th}$ PHD, i.e., PHD4, which could hydroxylate HIF-α when it was expressed at a high level.

According to inhibition mechanism of proline hydroxylase, they are roughly classified into two groups, i.e., iron chelating agents or iron competitive agents and 2-ketoglutaric acid analogues. Iron chelating agents or iron competitive agents can bind to $Fe^{2+}$ binding site of ODDD, thereby preventing HIF-α from binding to proline hydroxylase (e.g., prolyl-4-hydroxyases; EC 1.14.11.2), terminating hydroxylation reaction, avoiding degradation of HIF-α, and achieving stabilization of HIF-α. 2-Ketoglutaric acid analogues are compounds capable of inhibiting proline hydroxylase via competition with endogenous 2-oxoglutarate (2-OG), and currently, these inhibitors for proline hydroxylase are research focus.

At present, hot research relates to synthesizing peroral small molecular inhibitors for proline hydroxylase, to stabilize HIF-1a, and thus upregulating its downstream target genes, including but not being limited to erythropoietin (EPO), hemeoxygenase-1, adiponectin inducible nitric oxide synthase), etc., thereby achieving purpose of treating diseases such as anemia, acute ischemic reperfusion injury, etc.

CONTENTS OF THE INVENTION

The inventors of the present invention obtained via deep researches and inventive works a substituted acethydrazide derivative, i.e., a compound of Formula I. The inventors surprisingly found this compound or a pharmaceutically acceptable salt thereof could effectively inhibit proline hydroxylase, stabilize HIF-α, especially HIF-1α, and has potency in the manufacture of a medicament for treatment and/or prophylaxis and/or adjuvant therapy of diseases such as anemia, acute ischemic reperfusion injury. Hence, the following invention is provided:

One aspect of the present invention relates to a compound of Formula I, or a pharmaceutically acceptable salt thereof:

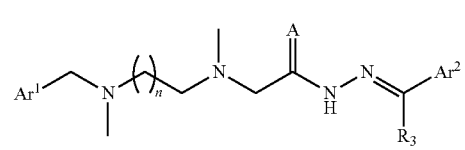

wherein:
n is 1, 2, 3, 4 or 5;
A is O or S;
$R_3$ is selected from hydrogen, and $C_1$-$C_4$ alkyl;
$Ar^1$ is an aryl substituted with $R_1$, in which $R_1$ is selected from: hydrogen, $C_1$-$C_6$ alkyl, $C_1$-$C_6$ alkoxy, trifluoromethyl and cyano;
$Ar^2$ is an aryl substituted with $R_2$, $R_4$, and $R_5$, wherein $R_2$, $R_4$, and $R_5$ are independently selected from: hydrogen, hydroxy, $C_1$-$C_6$ alkyl, $C_1$-$C_6$ alkoxy, allyl, halogen and $C_1$-$C_4$ dialkylamino; wherein $R_2$, $R_4$, $R_5$ cannot be hydrogen simultaneously.

In the proviso that $R_2$, $R_4$, and $R_5$ cannot be hydrogen simultaneously, any two or three of $R_2$, $R_4$ and $R_5$ can be the same or different.

In one embodiment of the present invention, $Ar^1$ is phenyl substituted with $R_1$, wherein $R_1$ is at ortho-position, para-position or meta-position.

In one embodiment of the present invention, $Ar^2$ is phenyl substituted with $R_2$, $R_4$, $R_5$, wherein $R_2$, $R_4$, $R_5$ are at ortho-position, para-position or meta-position.

With regard to the compound of any item of the present invention, or a pharmaceutically acceptable salt thereof, preferably, the $Ar^1$ or $Ar^2$ meets any one or more requirements of the following items (1)-(5):
(1) the aryl is selected from phenyl, naphthyl, anthracenyl, phenanthrenyl, indenyl, fluorenyl, and acenaphthenyl;
(2) the $C_1$-$C_6$ alkyl is $C_1$-$C_4$ alkyl; particularly, in any one of the above items, $C_1$-$C_6$ alkyl is independently $C_1$-$C_4$ alkyl;
(3) the $C_1$-$C_6$ alkoxy is $C_1$-$C_4$ alkoxy; particularly, in any one of the above items, $C_1$-$C_6$ alkoxy is independently $C_1$-$C_4$ alkoxy;
(4) the $C_1$-$C_4$ dialkylamino is $C_1$-$C_3$ dialkylamino;
(5) the halogen is selected from fluorine, chlorine, bromine, and iodine.

With regard to the compound or a pharmaceutically acceptable salt thereof according to any one of items of the present invention, preferably:

n is 1 or 2;

A is O;

$R_3$ is hydrogen;

$Ar^1$ is phenyl or naphthyl substituted with $R_1$, wherein $R_1$ is selected from: hydrogen, $C_1$-$C_4$ alkyl, methoxy, ethoxy, trifluoromethyl, and cyano;

$Ar^2$ is phenyl or naphthyl substituted with $R_2$, $R_4$, $R_5$, wherein $R_2$, $R_4$, and $R_5$ are independently selected from: hydrogen, hydroxy, $C_1$-$C_4$ alkyl, methoxy, ethoxy, allyl, halogen, dimethylamino, diethylamino and methylethylamino; wherein $R_2$, $R_4$, and $R_5$ cannot be hydrogen simultaneously.

According to any one of items of the present invention, for the compound or a pharmaceutically acceptable salt thereof, preferably, is the compound of Table 1 or a pharmaceutically acceptable salt thereof:

TABLE 1

Some compounds of the present invention

| No. | Name | Structure formula |
|---|---|---|
| 1 | (E)-N'-(3-methoxy-2-hydroxybenzal)-2-{N-{2-[N-(naphthalen-1-yl-methylene)-N-methylamino]ethyl}N-methylamino)acethydrazide | |
| 2 | (E)-N'-(3,5-di-tert-butyl-2-hydroxybenzal)-2-{N-{2-[N-(naphthalen-1-yl-methylene)-N-methylamino]ethyl}N-methylamino}acethydrazide | |
| 3 | (E)-N'-(3-ethoxy-2-hydroxybenzal)-2-{N-{2-[N-(naphthalen-1-yl-methylene)-N-methylamino]ethyl}N-methylamino}acethydrazide | |
| 4 | (E)-N'-[(2-hydroxynaphthalen-1-yl)methylene]-2-{N-{2-[N-(naphthalen-1-yl-methylene)-N-methylamino]ethyl}N-methylamino}acethydrazide | |
| 5 | (E)-N'-(4-N,N-diethylamino-2-hydroxybenzal)-2-{N-{2-[N-(naphthalen-1-yl-methylene)-N-methylamino]ethyl}N-methylamino}acethydrazide | |

TABLE 1-continued

Some compounds of the present invention

| No. | Name | Structure formula |
|---|---|---|
| 6 | (E)-N'-(3-bromo-4-hydroxybenzal)-2-{N-{2-[N-(naphthalen-1-yl-methylene)-N-methylamino]ethyl}N-methylamino}acethydrazide | |
| 7 | (E)-N'-(4-bromobenzal)-2-{N-{2-[N-(naphthalen-1-yl-methylene)-N-methylamino]ethyl}N-methylamino}acethydrazide | |
| 8 | (E)-N'-(3,5-di-tert-butyl-2-hydroxybenzal)-2-{N-{2-[N-(3-trifluoromethylbenzyl)-N-methylamino]ethyl}N-methylamino}acethydrazide | |
| 9 | (E)-N'-(3-ethoxy-2-hydroxybenzal)-2-{N-{2-[N-(3-trifluoromethylbenzyl)-N-methylamino]ethyl}N-methylamino}acethydrazide | |
| 10 | (E)-N'-(4-N,N-diethylamino-2-hydroxybenzal)-2-{N-{2-[N-(3-trifluoromethylbenzyl)-N-methylamino]ethyl}N-methylamino}acethydrazide | |

TABLE 1-continued

Some compounds of the present invention

| No. | Name | Structure formula |
| --- | --- | --- |
| 11 | (E)-N'-(2,3-dihydroxybenzal)-2-{N-{2-[N-(3-trifluoromethylbenzyl)-N-methylamino]ethyl}N-methylamino}acethydrazide | |
| 12 | (E)-N'-(3-methoxy-2-hydroxybenzal)-2-{N-{2-[N-(4-isopropylbenzyl)-N-methylamino]ethyl}N-methylamino}acethydrazide | |
| 13 | (E)-N'-[(3-ethoxy-2-hydroxybenzal)methylene]-2-{N-{2-[N-(4-isopropylbenzyl)-N-methylamino]ethyl}N-methylamino}acethydrazide | |
| 14 | (E)-N'-[(2-hydroxynaphthalen-1-yl)methylene]-2-{N-{2-[N-(4-isopropylbenzyl)-N-methylamino]ethyl}N-methylamino}acethydrazide | |
| 15 | (E)-N'-(3,5-di-tert-butyl-2-hydroxybenzal)-2-{N-{2-[N-(4-isopropylbenzyl)-N-methylamino]ethyl}N-methylamino}acethydrazide | |

TABLE 1-continued

Some compounds of the present invention

| No. | Name | Structure formula |
|---|---|---|
| 16 | (E)-N'-(4-N,N-diethylamino-2-hydroxybenzal)-2-{N-{2-[N-(4-isopropylbenzyl)-N-methylamino]ethyl}N-methylamino}acethydrazide | |
| 17 | (E)-N'-(2,3-dihydroxybenzal)-2-{N-{2-[N-(4-isopropylbenzyl)-N-methylamino]ethyl}N-methylamino}acethydrazide | |
| 18 | (E)-N'-(3-bromo-6-hydroxybenzal)-2-{N-{2-[N-(4-isopropylbenzyl)-N-methylamino]ethyl}N-methylamino}acethydrazide | |
| 19 | (E)-N'-(3-methoxy-2-hydroxybenzal)-2-{N-{2-[N-(3-methoxybenzyl)-N-methylamino]ethyl}N-methylamino}acethydrazide | |
| 20 | (E)-N'-(3,5-di-tert-butyl-2-hydroxybenzal)-3-(N-(2-(N-(4-tert-butylbenzyl)-N-methylamino)propyl)N-methylamino)acethydrazide | |

TABLE 1-continued

Some compounds of the present invention

| No. | Name | Structure formula |
|---|---|---|
| 21 | (E)-N'-[(2-hydroxynaphthalen-1-yl)methylene]-2-{N-{2-[N-(3-methoxybenzyl)-N-methylamino]ethyl}N-methylamino}acethydrazide | |
| 22 | (E)-N'-(3,5-di-tert-butyl-2-hydroxybenzal)-2-{N-{2-[N-(3-methoxybenzyl)-N-methylamino]ethyl}N-methylamino}acethydrazide | |
| 23 | (E)-N'-(4-N,N-diethylamino-2-hydroxybenzal)-2-{N-{2-[N-(3-methoxybenzyl)-N-methylamino]ethyl}N-methylamino}acethydrazide | |
| 24 | (E)-N'-(2,3-dihydroxybenzal)-2-{N-{2-[N-(3-methoxybenzyl)-N-methylamino]ethyl}N-methylamino}acethydrazide | |
| 25 | (E)-N'-(3-bromo-6-hydroxybenzal)-2-{N-{2-[N-(3-methoxybenzyl)-N-methylamino]ethyl}N-methylamino}acethydrazide | |

TABLE 1-continued

Some compounds of the present invention

| No. | Name | Structure formula |
|-----|------|-------------------|
| 26 | (E)-N'-[(2-hydroxynaphthalen-1-yl)methylene]-2-{N-{2-[N-(4-cyanobenzyl)-N-methylamino]ethyl}N-methylamino}acethydrazide | |
| 27 | (E)-N'-(3,5-di-tert-butyl-2-hydroxybenzal)-2-{N-{2-[N-(4-cyanobenzyl)-N-methylamino]ethyl}N-methylamino}acethydrazide | |
| 28 | (E)-N'-(3-methoxy-2-hydroxybenzal)-2-{N-{2-[N-(4-cyanobenzyl)-N-methylamino]ethyl}N-methylamino}acethydrazide | |
| 29 | (E)-N'-(3-ethoxy-2-hydroxybenzal)-2-{N-{2-[N-(4-cyanobenzyl)-N-methylamino]ethyl}N-methylamino}acethydrazide | |
| 30 | (E)-N'-(4-N,N-diethylamino-2-hydroxybenzal)-2-{N-{2-[N-(4-cyanobenzyl)-N-methylamino]ethyl}N-methylamino}acethydrazide | |

TABLE 1-continued

Some compounds of the present invention

| No. | Name | Structure formula |
|---|---|---|
| 31 | (E)-N'-(3-methoxy-2-hydroxybenzal)-2-{N-{2-[N-(4-tert-butylbenzyl)-N-methylamino]ethyl}N-methylamino}acethydrazide | |
| 32 | (E)-N'-(3-ethoxy-2-hydroxybenzal)-2-{N-{2-[N-(4-tert-butylbenzyl)-N-methylamino]ethyl}N-methylamino}acethydrazide | |
| 33 | (E)-N'-(4-N,N-diethylamino-2-hydroxybenzal)-2-{N-{3-[N-(4-tert-butylbenzyl)-N-methylamino]propyl}N-methylamino}acethydrazide | |

Another aspect of the present invention relates to a method for preparing the compound of Formula I according to any one of items of the present invention, comprising the following steps:

1) dissolving N,N'-dimethylethanediamine or N,N'-dimethylpropanediamine in tetrahydrofuran, heating to reflux, then slowly adding benzyl chloride dropwise, generating and separating a compound of Formula 1;

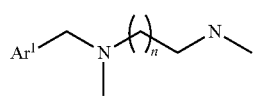

2) adding the compound of Formula 1, NaHCO₃ into acetone, refluxing, then adding methyl chloracetate or methyl chloroethanesulfonate, generating and separating a compound of Formula 2;

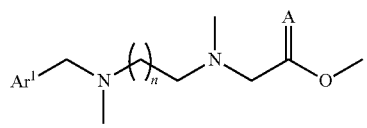

3) using ethanol as solvent, adding hydrazine hydrate or a corresponding substituted hydrazine, refluxing and then adding dropwise the compound of Formula 2, performing hydrazinolysis to generate a compound of Formula 3;

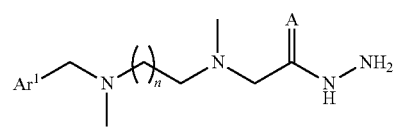

4) reacting the compound of Formula 3 with a corresponding salicylic aldehyde or aromatic ketone to generate a compound of Formula I;

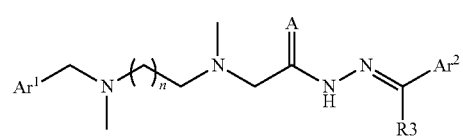

wherein all notations have the same meanings as stated in any of the above items of the present invention.

For the preparation method according to any item of the present invention preferably, it is characterized in any one or more of following items (1) to (3):

(1) in step 1), the molar ratio of benzyl chloride to N,N'-dimethylethanediamine or N,N'-dimethylpropanediamine is 1:6 (gradually generating white precipitate);

(2) in step 1), the reaction is monitored by using TLC;

(3) in step 1), after the benzyl chloride is completely reacted, heating is stopped, cooling is performed and then rotary evaporation is conducted to dry out the solvent, the products is washed by using NaOH aqueous solution, then is extracted by using $CH_2Cl_2$ and a pH≥12 is maintained during extraction; organic layers are combined and is subjected to column chromatography to obtain the compound of Formula 1.

Further another aspect of the present invention relates to a pharmaceutical composition, which comprises the compound of any one of items of the present invention or a pharmaceutically acceptable salt thereof, and at least one pharmaceutically acceptable excipient.

For the compound of any one of items of the present invention or a pharmaceutically acceptable salt thereof, or the pharmaceutical composition of the present invention, preferably, it is used or acts as a medicament.

For the compound of any one of items of the present invention or a pharmaceutically acceptable salt thereof, or the pharmaceutical composition of the present invention, preferably, it is used to inhibit proline hydroxylase or stabilize HIF-1, or used for treatment and/or prophylaxis and/or adjuvant therapy of anemia, acute ischemic reperfusion injury; preferably, the proline hydroxylase is prolyl-4-hydroxylases or EC 1.14.11.2; preferably, the HIF-1 is HIF-α; more preferably, the HIF-α is HIF-1α, HIF-2α, or HIF-3α.

The pharmaceutically acceptable salts, or the pharmaceutical composition of the present invention, which is used for upregulating erythropoietin, heme oxygenase-1 and/or adiponectin.

Further another aspect of the present invention relates to a use of the compound of any one of items of the present invention or a pharmaceutically acceptable salt thereof in the manufacture of a medicament for inhibiting proline hydroxylase or stabilizing HIF-1, or in the manufacture of a medicament for treatment and/or prophylaxis and/or adjuvant therapy of anemia, acute ischemic reperfusion injury; preferably, the HIF-1 is HIF-1α.

Further another aspect of the present invention relates to a use of the compound of any one of items of the present invention or a pharmaceutically acceptable salt thereof in the manufacture of a medicament for upregulating erythropoietin, heme oxygenase-1 and/or adiponectin.

Further another aspect of the present invention relates to a method for inhibiting proline hydroxylase or stabilizing HIF-1 in vivo or in vitro, comprising a step of using an effective amount of the compound of any one of items of the present invention or a pharmaceutically acceptable salt thereof; preferably, the HIF-1 is HIF-1α. In one embodiment of the present invention, the method is for non-treatment purpose.

Further another aspect of the present invention relates to a method for treatment and/or prophylaxis and/or adjuvant therapy of anemia, acute ischemic reperfusion injury, comprising a step of using an effective amount of the compound of any one of items of the present invention or a pharmaceutically acceptable salt thereof.

Those skilled in the art would be aware of that the compounds of the present invention can be used in form of their pharmaceutically acceptable salts. More specific examples of suitable acid salts include salts of hydrochloric acid, hydrobromic acid, sulfuric acid, phosphoric acid, nitric acid, perchloric acid, fumaric acid, acetic acid, propionic acid, succinic acid, glycolic acid, formic acid, lactic acid, maleic acid, tartaric acid, citric acid, pamoic acid, malonic acid, hydroxy maleic acid, phenylacetic acid, glutamic acid, benzoic acid, salicylic acid, fumaric acid, toluenesulfonic acid, methanesulfonic acid, naphthalene-2-sulfonic acid, benzenesulfonic acid, hydroxy naphthoic acid, hydroiodic acid, malic acid, steroic, tannic acid, etc. Other acids such as oxalic acid are not pharmaceutically acceptable, but can be used for preparing intermediate salts which can be used for obtaining the compounds of the present invention and their pharmaceutically acceptable salts. More specific suitable alkaline salts include salts of sodium, lithium, potassium, magnesium, aluminum, calcium, zinc, N,N'-dibenzylethanediamine, chloro-procaine, choline, diethanol amine, ethylenediamine, N-methylglucosamine and procaine.

The pharmaceutical composition of the present invention comprises an effective amount of the compound of Formula I of the present invention or its pharmaceutically acceptable salt, and one or more suitable excipients. Herein, the excipients include but are not limited to: ion exchangers, aluminum oxide, aluminum stearate, lecithin, serum protein such as human albumin, buffering agents such as phosphates, glycerol, sorbic acid, potassium sorbate, mixture of partial glycerides of saturated vegetable fatty acids, water, salts or electrolytes, such as protamine sulfate, disodium hydrogen phosphate, potassium hydrogen phosphate, sodium chloride, zinc salts, colloidal silicon dioxide, magnesium trisilicate, polyvinylpyrrolidone, celluloses, polyethylene glycol, sodium carboxymethylcellulose, polyacrylates, bee wax, lanolin.

The pharmaceutical composition of the compound of the present invention can be administered in any of the following ways: oral administration, spray inhalation, intrarectal administration, nasal administration, buccal administration, local administration, parenteral administration such as subcutaneous, intravenous, intramuscular, intraperitoneal, intrathecal, intraventricular, intrathoracic or intracranial injection or perfusion, or administration via implanted reservoirs, in which oral administration, intraperitoneal or intravenous injection are preferable.

In oral administration, the compound of the present invention can be processed in any preparation dosage forms suitable for oral administration, including but not being limited to tablets, capsules, aqueous solutions or aqueous suspensions, in which carriers of tablets usually include lactose and corn starch, and lubricants such as magnesium stearate may also be added. Diluents of capsules usually include lactose and dry corn starch. In aqueous suspensions, active ingredient is usually used together with suitable emulsifying agents and suspending agents. If required, the above dosage forms for oral administration may further be added with some sweeting agents, fragrances or coloring agents.

In local administration, especially local administration for treatment of neurologic diseases at easily reached surfaces or organs such as eyes, skin or lower intestinal tract, the compound of the present invention can be processed in different dosage forms for local administration according to different disease surfaces or organs, which is specifically illustrated as follows:

In local administration for eyes, the compound of the present invention can be formulated to form a dosage form of micronized suspension or solution, wherein the used carrier is isotonic sterile saline with a certain pH, in which preservative such as chlorobenzyl alkoxide may be added or not. For eye uses, the compound can be in ointment form such as vaseline ointment.

In local administration for skin, the compound of the present invention can be formulated to form suitable dosage forms such as ointments, lotions or creams, wherein the active ingredient is suspended or dissolved in one or more carriers. The ointments can use carriers including but not being limited to: mineral oil, liquid vaseline, white vaseline, propylene glycol, polyoxyethylene, polyoxypropylene, emulsified wax and water; the carriers usable in lotions or creams include but are not limited to: mineral oil, sorbitan monostearate, Tween-60, cetyl ester wax, hexadecene aromatic alcohol, 2-octyldodecanol, benzyl alcohol, and water.

The compound of the present invention can further be administered in sterile injection dosage form, including sterile injection water or oil suspension or sterile injection solution, wherein the usable carriers and solvents include water, Ringer's solution and isotonic NaCl solution. In addition, sterilized non-volatile oils such as monoglyceride or diglyceride can also be used as solvents or suspending media.

It should be further pointed out that dosage and usage of the compound of the present invention depend on many factors, including patient's age, body weight, gender, natural health conditions, nutritional status, activity strength of compound, administration time, metabolism rate, severity of disorder and attending doctor's subjective judgement. The preferable dosage is between 0.01 and 100 mg/kg of body weight per day, in which the optimal dosage is 5 to 10 mg/kg of body weight per day.

In the present invention,

The term "$C_1$-$C_6$ alkyl" refers to a straight or branched alkyl having 1-4 carbon atoms, for example, methyl, ethyl, propyl, isopropyl, n-butyl, sec-butyl, tert-butyl, pentyl, 2-pentyl, isopentyl, neopentyl, hexyl, 2-hexyl, 3-hexyl, etc.; $C_1$-$C_4$ alkyl, $C_1$-$C_3$ alkyl or $C_1$-$C_2$ alkyl can be interpreted similarly. Specific alkyl can be $C_1$-$C_4$ alkyl, $C_1$-$C_3$ alkyl or $C_1$-$C_2$ alkyl.

The term "$C_1$-$C_4$ alkoxy" refers to a straight or branched alkoxy having 1-4 carbon atoms, for example, methoxy, ethoxy, propoxy, isopropoxy, n-butoxy, sec-butoxy, tert-butoxy, pentoxy, 2-pentoxy, isopentoxy, neo-pentoxy, hexyloxy, 2-hexyloxy, 3-hexyloxy, etc.; $C_1$-$C_4$ alkoxy, $C_1$-$C_3$ alkoxy or $C_1$-$C_2$ alkoxy can be interpreted similarly. Specific alkoxy is $C_1$-$C_4$ alkoxy, $C_1$-$C_3$ alkoxy or $C_1$-$C_2$ alkoxy.

The term "halogen" refers to fluorine, chlorine, bromine and iodine atoms.

The term "aryl" refers to aromatic carboatomic ring having monocyclic ring (e.g., phenyl), polycyclic ring (e.g., xenyl) or multi-fused ring in which at least one ring is aromatic ring (e.g., 1, 2, 3, 4-tetrahydronaphthyl, naphthyl), which is optionally mono-, di- or tri-substituted with, for example, halogen, lower alkyl, lower alkoxy, trifluoromethyl, aryl, heteroaryl and hydroxy.

The term "arylalkyl" refers to an alkyl (as defined above) substituted with one or more aryls (as defined above). Preferably, arylalkyl refers to aryl-$C_1$-$C_3$ alkyl. Examples include benzyl, phenylethyl, etc.

The term "halogen" refers to fluorine, chlorine, bromine and iodine atoms.

The term "$C_1$-$C_4$ dialkylamino" can be $C_1$-$C_3$ dialkylamino or $C_1$-$C_2$ dialkylamino. Specific examples include dimethylamino, diethylamino, methylethylamino, di-n-propylamino or di-iso-propylamino.

In the present invention, if not specifically defined, the meaning of "stabilizing" is "not being degraded"; preferably, refers to "not being degraded by proline hydroxylase".

In the present invention, if not specifically defined, the proline hydroxylase refers to prolyl-4-hydroxylases or EC 1.14.11.2.

In the present invention, if not specifically defined, the HIF-1 is HIF-α; preferably, the HIF-α is HIF-1α, HIF-2α or HIF-3α.

SPECIFIC MODELS FOR CARRYING OUT THE INVENTION

The embodiments of the present invention are illustrated in details in conjunction with examples. However, those skilled in the art would understand the following examples are merely to illustrate the present invention, rather than to limit the scope of the present invention. When specific conditions are not given in the examples, conventional conditions or conditions recommended by manufacturers are applied. The reagents or instruments which manufactures are not given are all conventional products commercially available in markets.

Melting points of compounds are measured by YRT-3 type melting point instrument, in which temperatures are not calibrated. $^1$H-NMR spectra are measured by Bruker ARX 400 type NMR spectrometer. FAB mass spectra are measured by Zabspect high resolution magnetic mass spectrometer.

Preparation of Intermediates

Preparation Example 1: Intermediate 1

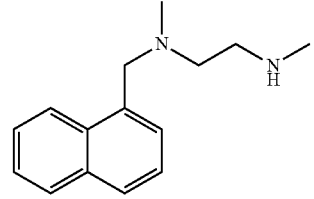 [SMILES: CNCCN(C)Cc1cccc2ccccc12]

9.6 mL (0.36 mol) of N,N'-dimethylethanediamine and 100 mL of tetrahydrofuran were added to a three-necked bottle equipped with constant pressure funnel, reflux condensing tube and thermometer, mixed evenly and then heated. When the reaction solution was slightly boiled (about 56° C.), 10 g (0.06 mol) of 1-chloromethylnaphthalene was slowly added in dropwise to the reaction solution, white precipitate was gradually generated, and thin-layer chromatography (TLC) was used to monitor the end of reaction. When the spot of 1-chloromethylnaphthalene in the reaction solution disappeared on thin-layer chromatography, heating was stopped, cooling was carried out, solvent was dried out by rotary evaporation, 3 mol/L of sodium hydroxide solution was used for washing, dichloromethane was used for extracting the washing liquid in which pH≥12 was maintained during extraction, all organic phases were combined, separated by silica column (eluent: dichloromethane/methanol=20/1) to Obtain {[N-(naphthalen-1-yl-methylene)-N-methylamino]ethyl}N'-methylamino, light yellow liquid, yield 86%. 1H-NMR (400 MHz, CDCl3) δ: 8.18 (7H, m), 4.10 (2H, s), 3.26 (3H, s), 2.50 (4H, m), 2.26 (3H, s); ELMS (m/z): 229.2[M+H]$^+$.

Preparation Example 2: Intermediate 2

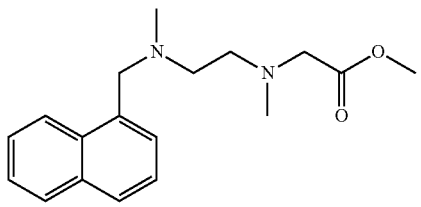 [SMILES: COC(=O)CN(C)CCN(C)Cc1cccc2ccccc12]

3.56 g (0.02 mol) of {[N-(naphthalen-1-yl-methylene)-N-methylamino]ethyl}N'-methylamine and 2.1 g (0.025 mol) of sodium hydrogen carbonate were added to 100 mL three-necked bottle equipped with constant pressure funnel, reflux condensing tube and thermometer, then 40 mL acetone was added, mixed evenly and then heated to reflux, 2.36 g (0.022 mol) of methyl acetate was slowed added in dropwise to the reaction solution, thin-layer chromatography (TLC) was used to monitor the end of reaction. When the spot of {[N-(naphthalen-1-yl-methylene)-N-methylamino]ethyl}N'-methylamine in the reaction solution disappeared on thin-layer chromatography, heating was stopped, cooling was carried out, solvent was dried out by rotary evaporation, silica column separation was carried out (eluent: ethyl acetate/petroleum=1/3) to obtain methyl 2-{N-{2-[N-(naphthalen-1-yl-methylene)-N-methylamino]ethyl}N-methylamino}acetate, light yellow liquid, yield 85%. 1H-NMR (400 MHz, CDCl3) δ: 8.18 (7H, m), 4.10 (2H, s), 3.68 (3H, s), 3.32 (2H, s), 2.37 (4H, m), 2.26 (6H, s); EI-MS (m/z): 301.2[M+H]+.

Preparation Example 3: Intermediate 3

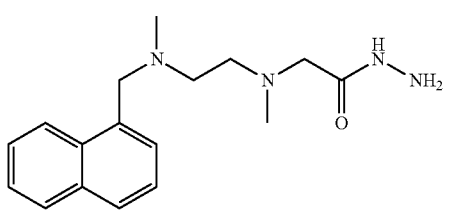 [SMILES: CN(CCN(C)Cc1cccc2ccccc12)CC(=O)NN]

2.1 g (0.06 mol) of 85% hydrazine hydrate and 50 ml of anhydrous ethanol were added to 250 mL three-necked bottle equipped with constant pressure funnel, reflux condensing tube and thermometer, mixed evenly and then heated to reflux, 5.0 g (0.02 mol) of methyl 2-{N-{2-[N-(naphthalen-1-yl-methylene)-N-methylamino]ethyl}N-methylamino}acetate was slowly added to the reaction solution, and reacted for 2 h, then heating was stopped, cooling was carried out, solvent was dried out by rotary evaporation, silica column separation was carried out (eluent: dichloromethane/methanol=10/1) to obtain 2-{N-{2-[N-(naphthalen-1-yl-methylene)-N-methylamino]ethyl}N-methylamino}acethydrazide, white solid, yield 86%. 1H-NMR (400 MHz, CDCl3) δ: 8.18 (7H, m), 4.10 (2H, s), 3.29 (2H, s), 2.37 (4H, m), 2.26 (6H, s); EI-MS (m/z): 301.2[M+H]+.

Preparation Example 4: Intermediate 4

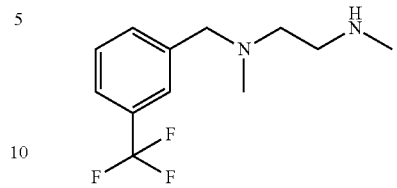

Pare- and meta-trifluoromethylbenzyl chloride was used as raw material, and operations were the same for Intermediate 1. Light yellow liquid product was obtained. MS [M]+=246.1 m/e.

Preparation Example 5: Intermediate 5

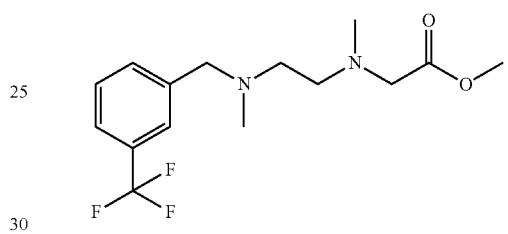

Intermediate 4 was used as raw material, and operations were the same for Intermediate 2. Light yellow liquid product was obtained. MS [M]+=318.2 m/e.

Preparation Example 6: Intermediate 6

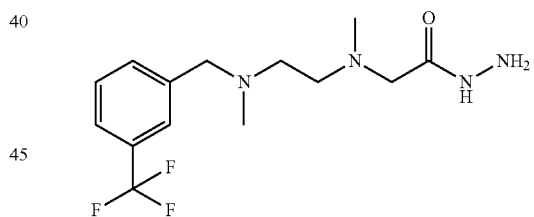

Intermediate 5 was used as raw materials, and operations were the same for Intermediate 3. Light yellow liquid product was obtained. MS [M]+=318.2 m/e.

Preparation Example 7: Intermediate 7

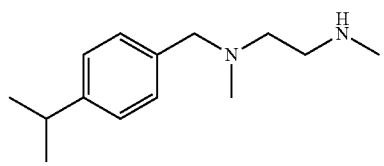 [SMILES: CNCCN(C)Cc1ccc(C(C)C)cc1]

4-Isopropylbenzyl chloride was used as raw material, and operations were the same for Intermediate 1. Light yellow liquid product was obtained. MS [M]+=220.2 m/e.

Preparation Example 8: Intermediate 8

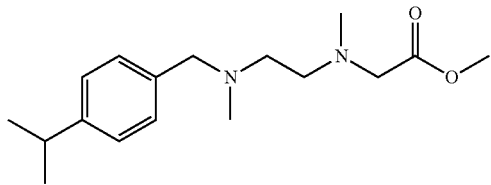 [SMILES: COC(=O)CN(C)CCN(C)Cc1ccc(C(C)C)cc1]

Intermediate 7 was used as raw material, and operations were the same for Intermediate 2. Light yellow liquid product was obtained. MS [M]$^+$=292.2 m/e.

Preparation Example 9: Intermediate 9

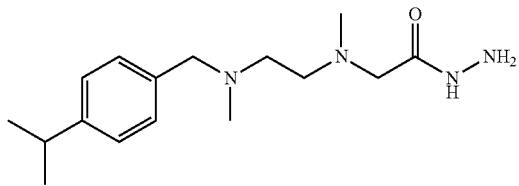 [SMILES: CC(C)c1ccc(CN(C)CCN(C)CC(=O)NN)cc1]

Intermediate 8 was used as raw material, and operations were the same for Intermediate 3. Light yellow liquid product was obtained. MS [M]$^+$=292.2 m/e.

Preparation Example 10: Intermediate 10

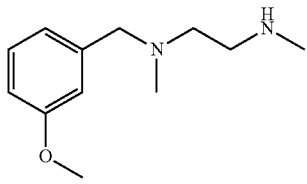

3-methoxybenzyl chloride was used as raw material, and operations were the same for Intermediate 1. Light yellow liquid product was obtained. MS [M]$^+$=208.2 m/e.

Preparation Example 11: Intermediate 11

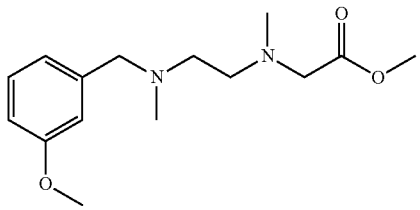 [SMILES: COC(=O)CN(C)CCN(C)Cc1cccc(OC)c1]

Intermediate 10 was used as raw material, and operations were the same for Intermediate 2. Light yellow liquid product was obtained. MS [M]$^+$=280.2 m/e.

Preparation Example 12: Intermediate 12

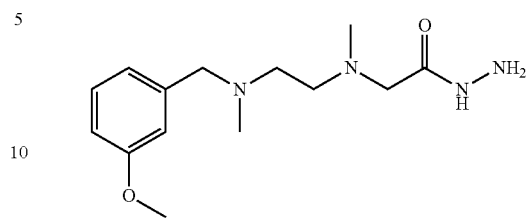

Intermediate 11 was used as raw material, and operations were the same for Intermediate 3. Yellow liquid product was obtained. MS [M]$^+$=280.2 m/e.

Preparation Example 13: Intermediate 13

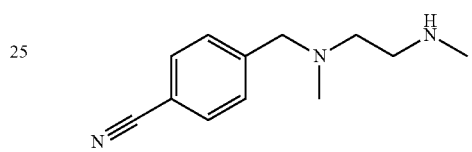

4-(Bromo-methyl)benzonitrile was used as raw material, and operations were the same for Intermediate 1. Light yellow liquid product was obtained. MS [M]$^+$=203.1 m/e.

Preparation Example 14: Intermediate 14

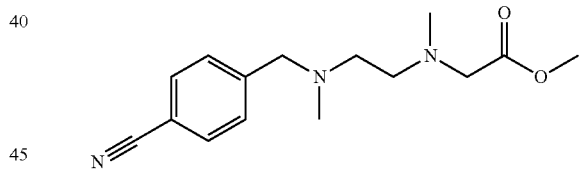

Intermediate 13 was used as raw material, and operations were the same for Intermediate 2. Light yellow liquid product was obtained. MS [M]$^+$=275.2 m/e.

Preparation Example 15: Intermediate 15

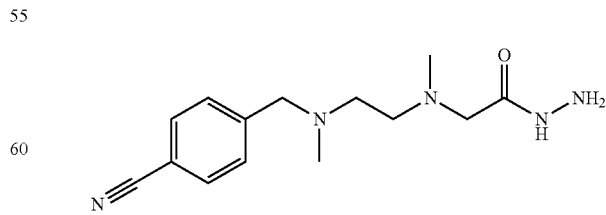

Intermediate 14 was used as raw material, and operations were the same for Intermediate 3. Yellow liquid product was obtained. MS [M]$^+$=275.2 m/e.

Preparation Example 16: Intermediate 16

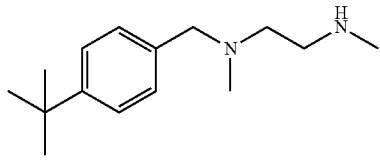 [SMILES: CNCCN(C)Cc1ccc(C(C)(C)C)cc1]

4-tert-butylbenzyl chloride was used as raw material, and operations were the same for Intermediate 1. Light yellow liquid product was obtained. MS [M]$^+$=234.2 m/e.

Preparation Example 17: Intermediate 17

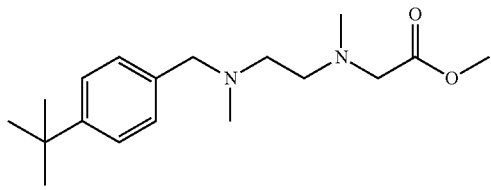 [SMILES: COC(=O)CN(C)CCN(C)Cc1ccc(C(C)(C)C)cc1]

Intermediate 16 was used as raw material, and operations were the same for Intermediate 2. Light yellow liquid product was obtained. MS [M]$^+$=306.2 m/e.

Preparation Example 18: Intermediate 18

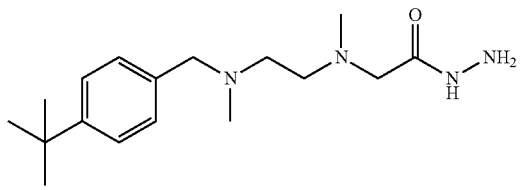 [SMILES: CN(CCN(C)Cc1ccc(C(C)(C)C)cc1)CC(=O)NN]

Intermediate 17 was used as raw material, and operations were the same for Intermediate 3. Yellow liquid product was obtained. MS [M]$^+$=306.2 m/e.

Preparation Example 19: Intermediate 19

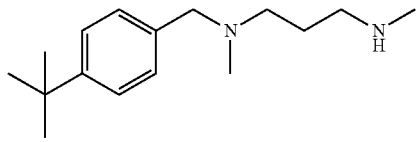 [SMILES: CNCCCN(C)Cc1ccc(C(C)(C)C)cc1]

Para-tert-butylbenzyl chloride and N,N'-dimethylpropanediamine were used as raw materials, and operations were the same for Intermediate 1. Light yellow liquid product was obtained. MS [M]$^+$=248.2 m/e.

Preparation Example 20: Intermediate 20

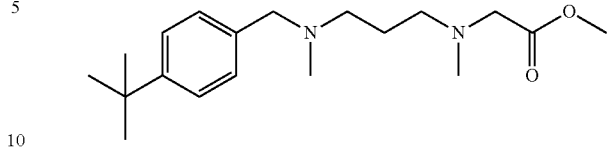

Intermediate 16 was used as raw material, and operations were the same for Intermediate 2. Light yellow liquid product was obtained. MS [M]$^+$=320.2 m/e.

Preparation Example 21: Intermediate 21

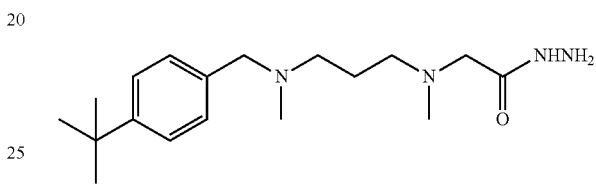

Intermediate 17 was used as raw material, and operations were the same for Intermediate 3. Light yellow liquid product was obtained. MS [M]$^+$=320.2 m/e.

Example 1: (E)-N'-(3-methoxy-2-hydroxybenzal)-2-{N-{2-[N-(naphthalen-1-yl-methylene)-N-methylamino]ethyl}N-methylamino}acethydrazide (Compound 1)

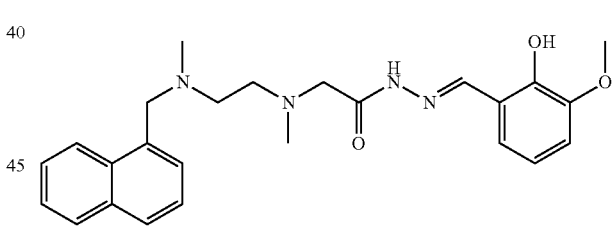

To 100 mL two-necked bottle equipped with thermometer and reflux condensing tube, 0.5 g (1.7 mmol) of Intermediate 3 and 20 mL of anhydrous ethanol were added, heated to reflux, 0.36 g (0.24 mmol) of ortho-vanilline was added in dropwise to the reaction solution, reacted for 2 h, then heating was stopped, cooling was carried out, solvent was dried out by rotary evaporation, silica column separation was carried out (eluent: dichloromethane/methanol=10/1) to obtain (E)-N'-(3-methoxy-2-hydroxybenzal)-2-{N-{2-[N-(naphthalen-1-yl-methylene)-N-methylamino]ethyl}N-methylamino}acethydrazide, white solid, yield 85%. $^1$H-NMR (400 MHz, DMSO-d6) δ: 11.30 (2H, m), 8.47 (1H, m), 7.84 (2H, m), 7.52 (4H, m), 6.80 (1H, m), 6.66 (1H, m), 6.36 (1H, s), 5.69 (1H, s), 4.01 (2H, s) 3.83 (3H, s), 3.30 (2H, s), 2.79 (4H, s), 2.61 (3H, s), 2.07 (3H, s); ELMS (m/z): 435.5[M+H]$^+$.

Example 2: (E)-N'-(3,5-di-tert-butyl-2-hydroxyben-
zal)-2-{N-{2-[N-(naphthalen-1-yl-methylene)-N-
methylamino]ethyl}N-methylamino}acethydrazide
(Compound 2)

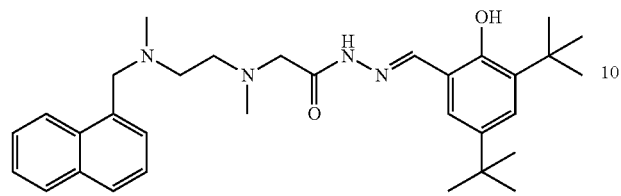

Intermediate 3 and 3,5-di-tert-butylsalicylic aldehyde were used as raw materials, and operations were the same for Example 1. White solid product was obtained. $^1$H-NMR (400 MHz, CDCl3) δ: 11.48 (1H, s), 11.26 (1H, s), 8.58 (1H, d, J=8.68 Hz), 7.90 (2H, m), 7.47 (4H, m), 7.21 (1H, s), 6.18 (1H, s), 5.75 (1H, s), 4.00 (2H, s), 3.34 (2H, s), 2.78 (4H, s), 2.68 (3H, s), 2.01 (3H, s), 1.32 (9H, s), 1.24 (9H, s); EI-MS (m/z): 517.6[M+H]$^+$.

Example 3: (E)-N'-(3-ethoxy-2-hydroxybenzal)-2-
{N-{2-[N-(naphthalen-1-yl-methylene)-N-methyl-
amino]ethyl}N-methylamino}acethydrazide (Compound 3)

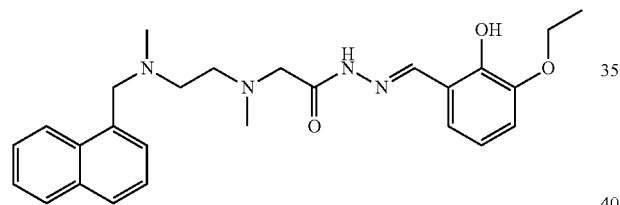

Intermediate 3 and 3-ethoxysalicylic aldehyde were used as raw materials, and operations were the same for Example 1. White solid product was obtained. $^1$H-NMR (400 MHz, CDCl3) δ: 11.25 (2H, m), 8.47 (1H, d, J=8.12 Hz), 7.90 (2H, m), 6.80 (1H, m), 6.62 (2H, m), 6.34 (1H, s), 5.70 (1H, d, J=7.56 Hz), 4.05 (4H, m), 3.30 (2H, m), 2.73 (4H, s), 2.57 (3H, s), 2.06 (3H, s), 1.43 (4H, m); ELMS (m/z): 449.5[M+H]$^+$.

Example 4: (E)-N'-[(2-hydroxynaphthalen-1-yl)
methylene]-2-{N-{2-[N-(naphthalen-1-yl-methyl-
ene)-N-methylamino]ethyl}N-
methylamino}acethydrazide (Compound 4)

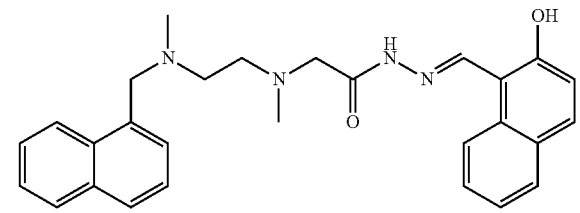 [SMILES: CN(CCN(C)Cc1cccc2ccccc12)CC(=O)N/N=C/c1c(O)ccc2ccccc12]

Intermediate 3 and 2-hydroxy-1-naphthaldehyde were used as raw materials, and operations were the same for Example 1. White solid product was obtained. $^1$H-NMR (400 MHz, CDCl3) δ: 12.62 (1H, s), 11.81 (1H, s), 8.71 (1H, d, J=8.12 Hz), 7.75 (8H, m), 7.26 (1H, m), 7.09 (3H, m), 6.02 (1H, d, J=8.68 Hz), 4.03 (2H, s), 3.42 (2H, s), 2.90 (2H, s), 2.70 (5H, m), 2.14 (3H, s); ELMS (m/z): 455.4[M+H]$^+$.

Example 5: (E)-N'-(4-N,N-diethylamino-2-hydroxy-
benzal)-2-{N-{2-[N-(naphthalen-1-yl-methylene)-N-
methylamino]ethyl}N-methylamino}acethydrazide
(Compound 5)

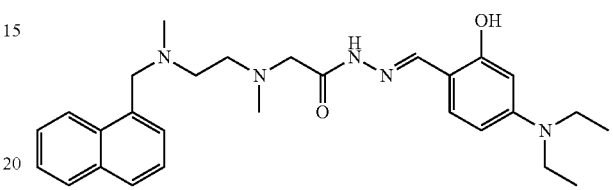

Intermediate 3 and 4-(diethylamino)salicylic aldehyde were used as raw materials, and operations were the same for Example 1. Light yellow solid product was obtained. $^1$H-NMR (400 MHz, CDCl3) δ: 11.08 (1H, s), 10.87 (1H, s), 8.49 (1H, d, J=8.32 Hz), 7.89 (2H, m), 7.48 (4H, m), 6.27 (1H, s), 6.08 (2H, m), 5.84 (1H, s), 3.98 (2H, s), 3.30 (6H, m), 2.72 (4H, s), 2.57 (3H, s), 2.04 (3H, s), 1.18 (6H, m); ELMS (m/z): 476.5[M+H]$^+$.

Example 6: (E)-N'-(3-bromo-4-hydroxybenzal)-2-
{N-{2-[N-(naphthalen-1-yl-methylene)-N-methyl-
amino]ethyl}N-methylamino}acethydrazide (Compound 6)

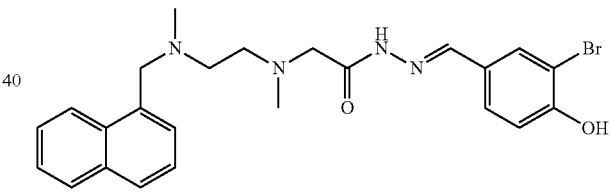

Intermediate 3 and 3-bromo-4-hydroxybenzaldehyde were used as raw materials, and operations were the same for Example 1. Light yellow solid product was obtained. $^1$H-NMR (400 MHz, CDCl3) δ: 11.02 (1H, s), 8.49 (1H, d, J=8.32 Hz), 7.94 (2H, m), 7.54 (4H, m), 6.92 (3H, m), 6.06 (1H, s), 4.00 (2H, s), 3.32 (2H, s), 2.72 (4H, s), 2.94 (3H, s), 2.03 (3H, s); EI-MS (m/z): 483.3[M+H]$^+$.

Example 7: (E)-N'-(4-bromobenzal)-2-{N-{2-[N-
(naphthalen-1-yl-methylene)-N-methylamino]
ethyl}N-methylamino}acethydrazide (Compound 7)

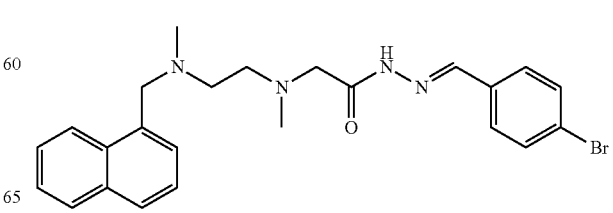

Intermediate 3 and p-bromobenzaldehyde were used as raw materials, and operations were the same for Example 1. Light yellow solid product was obtained. $^1$H-NMR (400 MHz, CDCl3) δ: 11.08 (1H, s), 8.49 (1H, d, J=8.32 Hz), 7.86 (2H, m), 7.52 (4H, m), 7.31 (2H, m), 6.81 (2H, m), 6.18 (1H, s), 3.98 (2H, s), 3.31 (2H, s), 2.70 (4H, s), 2.61 (3H, s), 2.03 (3H, s); EI-MS (m/z): 467.3[M+H]$^+$.

Example 8: (E)-N'-(3,5-di-tert-butyl-2-hydroxybenzal)-2-{N-{2-[N-(3-trifluoromethylbenzyl)-N-methylamino]ethyl}N-methylamino}acethydrazide (Compound 8)

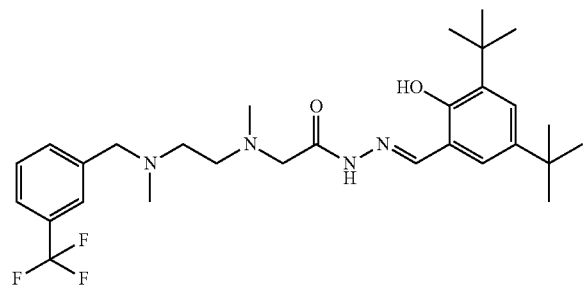 [SMILES: CN(CCN(C)Cc1cccc(C(F)(F)F)c1)CC(=O)N/N=C/c1cc(C(C)(C)C)cc(C(C)(C)C)c1O]

Intermediate 6 and 3,5-di-tert-butylsalicylic aldehyde were used as raw materials, and operations were the same for Example 1. White solid product was obtained. $^1$H-NMR (400 MHz, CDCl3) δ: 11.50 (1H, s), 11.25 (1H, s), 7.94 (1H, s), 7.67 (4H, m), 7.34 (1H, s), 6.69 (1H, s), 3.71 (2H, s), 3.28 (2H, s), 2.64 (2H, s), 2.53 (2H, s), 2.36 (3H, s), 2.25 (3H, s), 1.42 (9H, s), 1.24 (9H, s); ELMS (m/z): 535.5[M+H]$^+$.

Example 9: (E)-N'-(3-ethoxy-2-hydroxybenzal)-2-{N-{2-[N-(3-trifluoromethylbenzyl)-N-methylamino]ethyl}N-methylamino}acethydrazide (Compound 9)

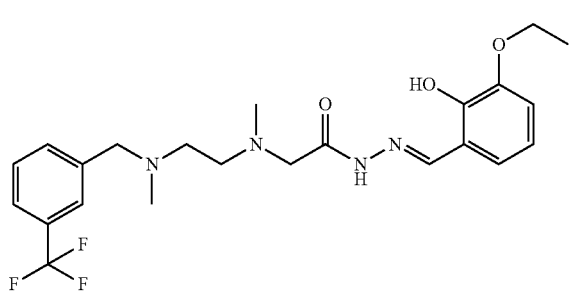 [SMILES: CCOc1cccc(/C=N/NC(=O)CN(C)CCN(C)Cc2cccc(C(F)(F)F)c2)c1O]

Intermediate 6 and 3-ethoxysalicylic aldehyde were used as raw materials, and operations were the same for Example 1. White solid product was obtained. $^1$H-NMR (400 MHz, CDCl3) δ: 11.43 (1H, s), 11.05 (1H, s), 8.10 (1H, s), 7.64 (4H, m), 6.90 (2H, m), 6.61 (1H, m), 4.13 (2H, m), 3.66 (2H, s), 3.25 (2H, s), 2.58 (4H, m), 2.29 (6H, m), 1.47 (3H, m); EI-MS (m/z): 467.3[M+H]$^+$.

Example 10: (E)-N'-(4-N,N-diethylamino-2-hydroxybenzal)-2-{N-{2-[N-(3-trifluoromethylbenzyl)-N-methylamino]ethyl}N-methylamino}acethydrazide (Compound 10)

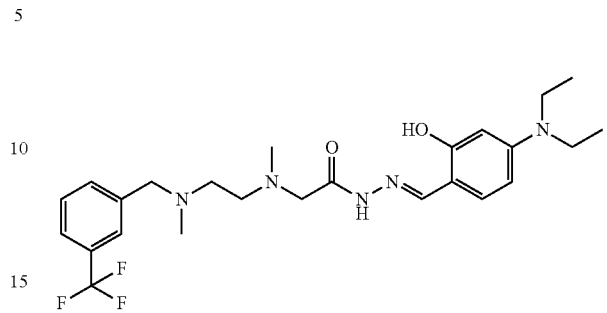

Intermediate 6 and 4-(diethylamino)salicylic aldehyde were used as raw materials, and operations were the same for Example 1. White solid product was obtained. $^1$H-NMR (400 MHz, CDCl3) δ: 11.20 (1H, s), 11.01 (1H, s), 7.87 (1H, s), 7.66 (4H, m), 6.71 (1H, m), 6.22 (2H, m), 6.19 (1H, s), 3.66 (2H, s), 3.38 (4H, m), 3.25 (2H, s), 2.61 (4H, m), 2.33 (6H, m), 1.20 (6H, m); EI-MS (m/z): 494.7[M±H]$^+$.

Example 11: (E)-N'-(2,3-dihydroxybenzal)-2-{N-{2-[N-(3-trifluoromethylbenzyl)-N-methylamino]ethyl}N-methylamino}acethydrazide (Compound 11)

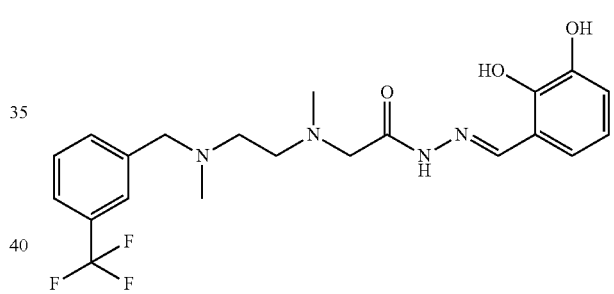

Intermediate 6 and 2,3-dihydroxybenzaldehyde were used as raw materials, and operations were the same for Example 1. White solid product was obtained. $^1$H-NMR (400 MHz, CDCl3) δ: 11.45 (2H, s), 7.80 (1H, s), 7.65 (4H, m), 6.95 (1H, m), 6.74 (1H, m), 6.42 (1H, m), 3.65 (1H, s), 3.28 (2H, s), 2.61 (4H, m), 2.34 (6H, m); EI-MS (m/z): 439.3[M+H]$^+$.

Example 12: (E)-N'-(3-methoxy-2-hydroxybenzal)-2-{N-{2-[N-(4-isopropylbenzyl)-N-methylamino]ethyl}N-methylamino}acethydrazide (Compound 12)

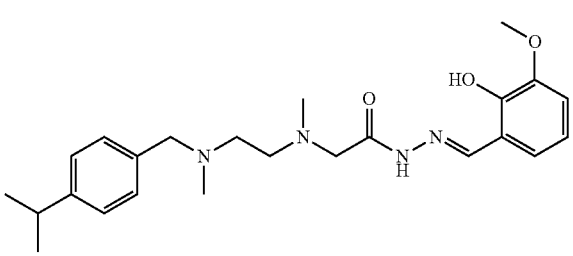 [SMILES: COc1cccc(/C=N/NC(=O)CN(C)CCN(C)Cc2ccc(C(C)C)cc2)c1O]

Intermediate 9 and ortho-vanilline were used as raw materials, and operations were the same for Example 1. White solid product was obtained. $^1$H-NMR (400 MHz, CDCl3) δ: 11.87 (1H, s), 11.39 (1H, s), 7.27 (5H, m), 6.86 (1H, m), 6.74 (1H, m), 6.40 (1H, m), 3.89 (3H, s), 3.57 (2H, m), 3.27 (2H, s), 2.89 (1H, m), 2.61 (4H, m), 2.38 (3H, s), 2.20 (3H, s), 1.25 (6H, s); ELMS (m/z): 427.3[M+H]$^+$.

Example 13: (E)-N'-[(3-ethoxy-2-hydroxybenzal) methylene]-2-{N-{2-[N-(4-isopropylbenzyl)-N-methylamino]ethyl}N-methylamino}acethydrazide (Compound 13)

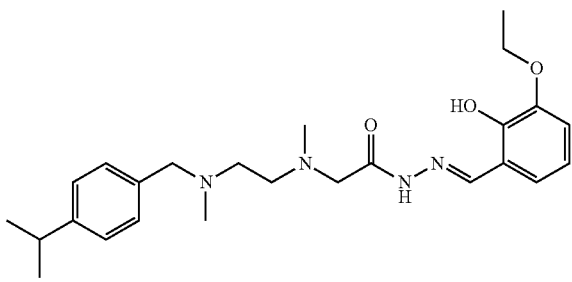 [SMILES: CCOc1cccc(/C=N/NC(=O)CN(C)CCN(C)Cc2ccc(C(C)C)cc2)c1O]

Intermediate 9 and 3-ethoxysalicylic aldehyde were used as raw materials, and operations were the same for Example 1. White solid product was obtained. $^1$H-NMR (400 MHz, CDCl3) δ: 11.84 (1H, s), 11.30 (1H, s), 7.70 (1H, s), 7.32 (4H, m), 6.89 (1H, m), 6.71 (1H, m), 6.39 (1H, m), 4.12 (2H, m), 3.56 (2H, s), 3.27 (2H, s), 2.90 (1H, m), 2.62 (4H, m), 2.38 (3H, s), 2.20 (3H, s), 1.48 (3H, m), 1.24 (6H, m); EI-MS (m/z): 441.6[M+H]$^+$.

Example 14: (E)-N'-[(2-hydroxynaphthalen-1-yl) methylene]-2-{N-{2-[N-(4-isopropylbenzyl)-N-methylamino]ethyl}N-methylamino}acethydrazide (Compound 14)

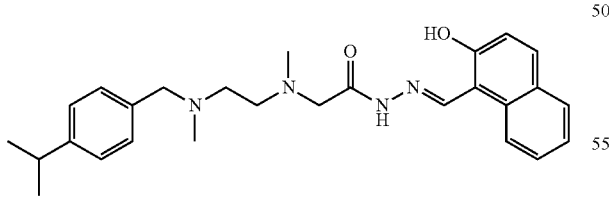

Intermediate 9 and 2-hydroxy-1-naphthaldehyde were used as raw materials, and operations were the same for Example 1. White solid product was obtained. $^1$H-NMR (400 MHz, CDCl3) δ: 12.70 (1H, s), 12.18 (1H, s), 8.76 (1H, s), 7.70 (2H, m), 7.38 (8H, m), 3.61 (2H, s), 3.32 (2H, s), 2.75 (1H, m), 2.66 (2H, m), 2.52 (2H, m), 2.41 (3H, s), 2.29 (3H, s), 1.08 (6H, m); EI-MS (m/z): 447.4[M+H]$^+$.

Example 15: (E)-N'-(3,5-di-tert-butyl-2-hydroxybenzal)-2-{N-{2-[N-(4-isopropylbenzyl)-N-methylamino]ethyl}N-methylamino}acethydrazide (Compound 15)

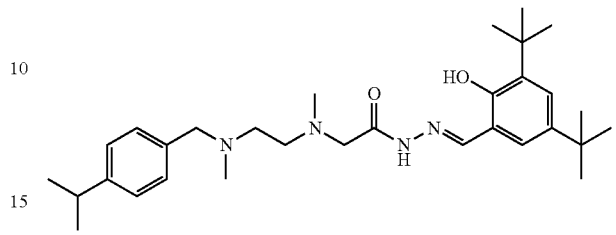

Intermediate 9 and 3,5-di-tert-butylsalicylic aldehyde were used as raw materials, and operations were the same for Example 1. White solid product was obtained. $^1$H-NMR (400 MHz, CDCl3) δ: 11.67 (2H, m), 7.78 (1H, s), 7.32 (3H, m), 7.23 (2H, m), 6.69 (1H, s), 3.57 (2H, s), 3.27 (2H, s), 2.87 (1H, m), 2.61 (2H, m), 2.43 (2H, m), 2.35 (3H, s), 2.25 (3H, s), 1.44 (9H, s), 1.27 (9H, s), 1.19 (6H, s); EI-MS (m/z): 509.6[M+H]$^+$.

Example 16: (E)-N'-(4-N,N-diethylamino-2-hydroxybenzal)-2-{N-{2-[N-(4-isopropylbenzyl)-N-methylamino]ethyl}N-methylamino}acethydrazide (Compound 16)

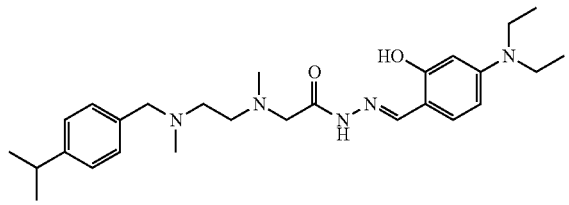 [SMILES: CCN(CC)c1ccc(/C=N/NC(=O)CN(C)CCN(C)Cc2ccc(C(C)C)cc2)c(O)c1]

Intermediate 9 and 4-(diethylamino)salicylic aldehyde were used as raw materials, and operations were the same for Example 1. White solid product was obtained. $^1$H-NMR (400 MHz, CDCl3) δ: 11.40 (1H, s), 11.23 (1H, s), 7.61 (1H, s), 7.32 (5H, m), 6.55 (1H, m), 6.19 (1H, s), 6.10 (1H, m), 3.55 (2H, s), 3.37 (4H, m), 3.23 (2H, s), 2.90 (1H, m), 2.59 (2H, s), 2.50 (2H, s), 2.36 (3H, s), 2.18 (3H, s), 1.25 (12H, m); ELMS (m/z): 468.5[M+H]$^+$.

Example 17: (E)-N'-(2,3-dihydroxybenzal)-2-{N-{2-[N-(4-isopropylbenzyl)-N-methylamino]ethyl}N-methylamino}acethydrazide (Compound 17)

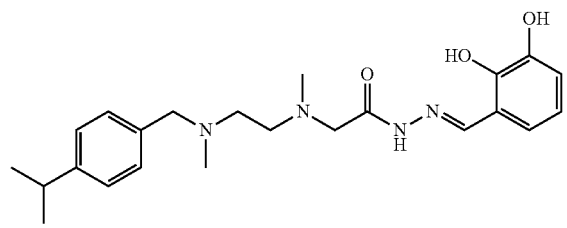 [SMILES: CC(C)c1ccc(CN(C)CCN(C)CC(=O)N/N=C/c2cccc(O)c2O)cc1]

Intermediate 9 and 2,3-dihydroxybenzaldehyde were used as raw materials, and operations were the same for Example 1. White solid product was obtained. $^1$H-NMR (400 MHz, CDCl3) δ: 11.91 (2H, m), 7.49 (1H, s), 7.32 (5H, m), 6.91 (1H, m), 6.68 (1H, m), 6.23 (1H, m), 3.55 (2H, s), 3.28 (2H, s), 2.91 (1H, m), 2.63 (4H, m), 2.42 (3H, s), 2.17 (3H, s), 1.26 (6H, m); EI-MS (m/z): 413.4[M+H]$^+$.

Example 18: (E)-N'-(3-bromo-6-hydroxybenzal)-2-{N-{2-[N-(4-isopropylbenzyl)-N-methylamino]ethyl}N-methylamino}acethydrazide (Compound 18)

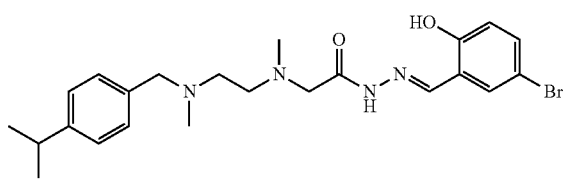 [SMILES: CC(C)c1ccc(CN(C)CCN(C)CC(=O)N/N=C/c2cc(Br)ccc2O)cc1]

Intermediate 9 and 3-bromo-6-hydroxybenzaldehyde were used as raw materials, and operations were the same for Example 1. Light yellow liquid product was obtained. $^1$H-NMR (400 MHz, CDCl3) δ: 12.04 (1H, s), 11.31 (1H, s), 7.31 (6H, m), 6.84 (2H, m), 3.54 (2H, s), 3.29 (2H, s), 2.95 (1H, m), 2.64 (2H, m), 2.57 (2H, m), 2.45 (3H, s), 2.18 (3H, s), 1.24 (6H, m); ELMS (m/z): 477.3[M+H]$^+$.

Example 19: (E)-N'-(3-methoxy-2-hydroxybenzal)-2-{N-{2-[N-(3-methoxybenzyl)-N-methylamino]ethyl}N-methylamino}acethydrazide (Compound 19)

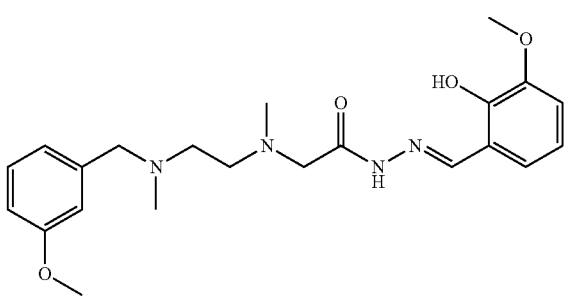 [SMILES: COc1cccc(CN(C)CCN(C)CC(=O)N/N=C/c2cccc(OC)c2O)c1]

Intermediate 12 and ortho-vanilline were used as raw materials, and operations were the same for Example 1. Light yellow solid product was obtained. $^1$H-NMR (400 MHz, CDCl3) δ: 11.74 (1H, s), 11.38 (1H, s), 7.84 (1H, s), 7.28 (1H, m), 6.96 (5H, m), 6.52 (1H, m), 3.91 (3H, s), 3.80 (3H, s), 3.58 (2H, s), 3.28 (2H, s), 2.62 (4H, m), 2.38 (3H, m), 2.25 (3H, s); EI-MS (m/z): 415.4[M+H]$^+$.

Example 20: (E)-N'-(3, 5-di-tert-butyl-2-hydroxybenzal)-3-(N-(2-(N-(4-tert-butylbenzyl)-N-methylamino)propyl)N-methylamino)acethydrazide (Compound 20)

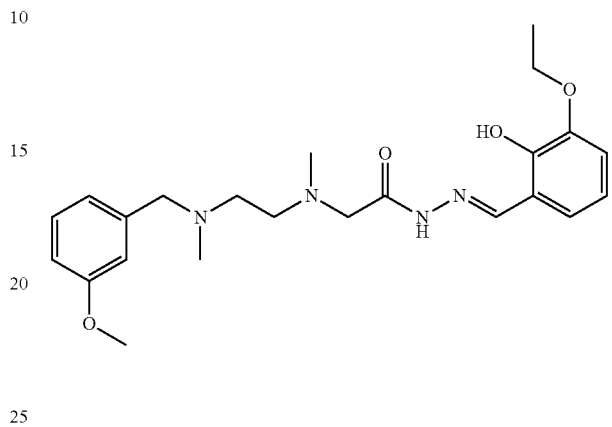

Intermediate 12 and 3-ethoxysalicylic aldehyde were used as raw materials, and operations were the same for Example 1. Light yellow solid product was obtained. $^1$H-NMR (400 MHz, CDCl3) δ: 11.70 (1H, s), 11.26 (1H, s), 7.81 (1H, s), 7.27 (1H, m), 6.97 (4H, m), 6.75 (1H, m), 6.51 (1H, m, 4.13 (2H, m), 3.76 (3H, s), 3.56 (2H, s), 3.26 (2H, s), 2.60 (4H, m), 2.36 (3H, s), 2.23 (3H, s), 1.48 (3H, m); ELMS (m/z): 429.4[M+H]$^+$.

Example 21: (E)-N'-[(2-hydroxynaphthalen-1-yl)methylene]-2-{N-{2-[N-(3-methoxybenzyl)-N-methylamino]ethyl}N-methylamino}acethydrazide (Compound 21)

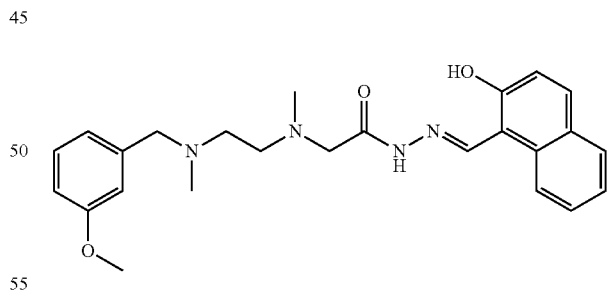

Intermediate 12 and 2-hydroxy-1-naphthaldehyde were used as raw materials, and operations were the same for Example 1. Light yellow solid product was obtained. $^1$H-NMR (400 MHz, CDCl3) δ: 12.70 (1H, s), 12.11 (1H, s), 8.76 (1H, s), 7.75 (2H, m), 7.31 (3H, m), 7.21 (4H, m), 6.82 (1H, m), 3.72 (3H, s), 3.61 (2H, s), 3.34 (2H, s), 2.72 (2H, m), 2.58 (2H, s), 2.46 (3H, s), 2.29 (3H, s); EI-MS (m/z): 435.5[M H]$^+$.

Example 22: (E)-N'-(3,5-di-tert-butyl-2-hydroxy-benzal)-2-{N-{2-[N-(3-methoxybenzyl)-N-methyl-amino]ethyl}N-methylamino}acethydrazide (Compound 22)

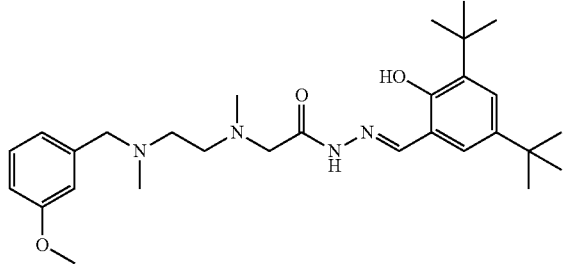 [SMILES: COc1cccc(CN(C)CCN(C)CC(=O)N/N=C/c2cc(C(C)(C)C)cc(C(C)(C)C)c2O)c1]

Intermediate 12 and 3,5-di-tert-butylsalicylic aldehyde were used as raw materials, and operations were the same for Example 1. Light yellow solid product was obtained. $^1$H-NMR (400 MHz, CDCl3) δ: 11.64 (2H, m), 7.65 (1H, s), 7.32 (2H, m), 6.99 (2H, m), 6.82 (1H, m), 6.56 (1H, s), 3.74 (3H, s), 3.55 (2H, s), 3.28 (2H, s), 2.64 (4H, m), 2.43 (3H, s), 2.21 (3H, s), 1.44 (9H, s), 1.30 (9H, s); ELMS (m/z): 497.6[M±H]$^+$.

Example 23: (E)-N'-(4-N,N-diethylamino-2-hydroxybenzal)-2-{N-{2-[N-(3-methoxybenzyl)-N-methylamino]ethyl}N-methylamino}acethydrazide (Compound 23)

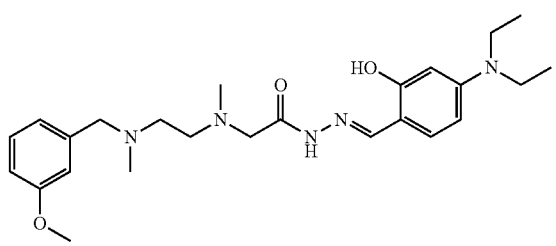 [SMILES: CCN(CC)c1ccc(/C=N/NC(=O)CN(C)CCN(C)Cc2cccc(OC)c2)c(O)c1]

Intermediate 12 and 4-(diethylamino)salicylic aldehyde were used as raw materials, and operations were the same for Example 1. Light yellow solid product was obtained. $^1$H-NMR (400 MHz, CDCl3) δ: 11.29 (2H, m), 7.69 (1H, s), 7.30 (1H, m), 6.97 (3H, m), 6.65 (1H, m), 6.20 (2H, m), 3.78 (3H, s), 3.56 (2H, s), 3.36 (4H, m), 3.23 (2H, s), 2.59 (4H, m), 2.35 (3H, s), 2.22 (3H, s), 1.18 (6H, m); EI-MS (m/z): 456.2 [M H]$^+$.

Example 24: (E)-N'-(2,3-dihydroxybenzal)-2-{N-{2-[N-(3-methoxybenzyl)-N-methylamino]ethyl}N-methylamino}acethydrazide (Compound 24)

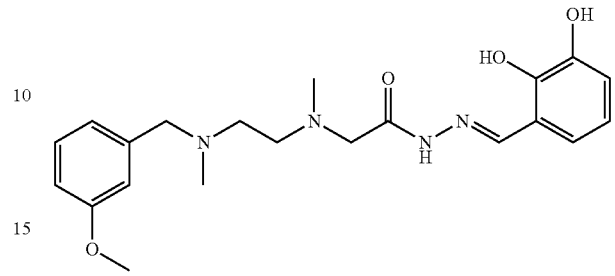

Intermediate 12 and 2,3-dihydroxybenzaldehyde were used as raw materials, and operations were the same for Example 1. Light yellow solid product was obtained. $^1$H-NMR (400 MHz, CDCl3) δ: 11.77 (2H, m), 7.55 (1H, s), 7.29 (1H, m), 6.99 (3H, m), 6.85 (1H, m), 6.75 (1H, m), 6.39 (1H, m), 3.76 (3H, s), 3.57 (2H, s), 3.29 (2H, s), 2.63 (4H, m), 2.41 (3H, s), 2.22 (3H, s); EI-MS (m/z): 401.3[M+H]$^+$.

Example 25: (E)-N'-(3-bromo-6-hydroxybenzal)-2-{N-{2-[N-(3-methoxybenzyl)-N-methylamino]ethyl}N-methylamino}acethydrazide (Compound 25)

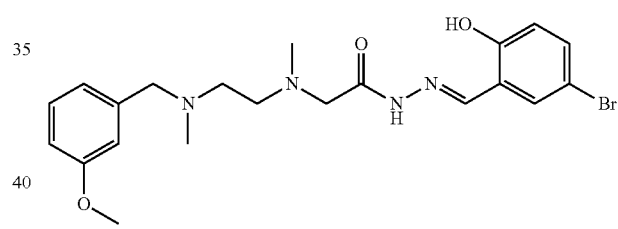

Intermediate 12 and 3-bromo-6-hydroxybenzaldehyde were used as raw materials, and operations were the same for Example 1. Light yellow solid product was obtained. $^1$H-NMR (400 MHz, CDCl3) δ: 11.81 (1H, s), 11.25 (1H, s), 7.34 (3H, m), 6.99 (7H, m), 3.80 (3H, s), 3.54 (2H, s), 3.28 (2H, s), 2.63 (4H, m), 2.44 (3H, s), 2.18 (3H, s); ELMS (m/z): 463.3[M+H]$^+$.

Example 26: (E)-N'-[(2-hydroxynaphthalen-1-yl)methylene]-2-{N-{2-[N-(4-cyanobenzyl)-N-methylamino]ethyl}N-methylamino}acethydrazide (Compound 26)

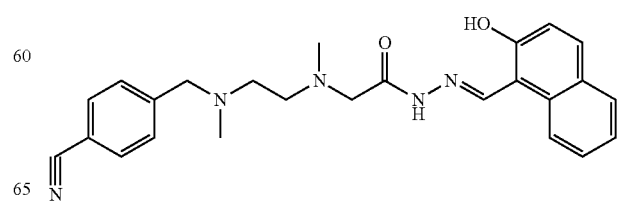

Intermediate 15 and 2-hydroxy-1-naphthaldehyde were used as raw materials, and operations were the same for Example 1. Light yellow solid product was obtained. ¹H-NMR (400 MHz, CDCl3) δ: 12.49 (1H, s), 11.46 (1H, s), 9.06 (1H, s), 7.76 (2H, m), 7.65 (2H, m), 7.55 (3H, m), 7.40 (2H, m), 7.22 (1H, m), 3.68 (2H, s), 3.33 (2H, s), 2.68 (2H, m), 2.55 (2H, m), 2.41 (3H, s), 2.29 (3H, s); ELMS (m/z): 430.4[M±H]⁺.

Example 27: (E)-N'-(3,5-di-tert-butyl-2-hydroxybenzal)-2-{N-{2-[N-(4-cyanobenzyl)-N-methylamino]ethyl}N-methylamino}acethydrazide (Compound 27)

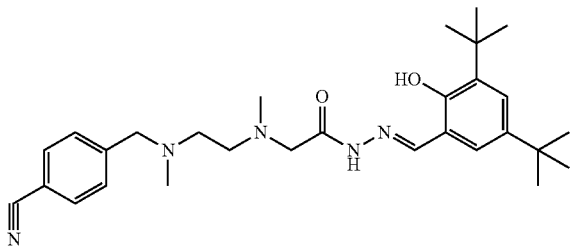 [SMILES: CN(CCN(C)Cc1ccc(C#N)cc1)CC(=O)N/N=C/c1cc(C(C)(C)C)cc(C(C)(C)C)c1O]

Intermediate 15 and 3,5-di-tert-butylsalicylic aldehyde were used as raw materials, and operations were the same for Example 1. Light yellow solid product was obtained. ¹H-NMR (400 MHz, CDCl3) δ: 11.44 (1H, s), 11.11 (1H, s), 8.11 (1H, s), 7.65 (2H, m), 7.51 (2H, m), 7.36 (1H, s), 6.75 (1H, s), 3.63 (2H, s), 3.27 (2H, s), 2.64 (4H, m), 2.36 (3H, s), 2.24 (3H, s), 1.43 (9H, s), 1.30 (9H, s); ELMS (m/z): 492.5 [M H]⁺.

Example 28: (E)-N'-(3-methoxy-2-hydroxybenzal)-2-{N-{2-[N-(4-cyanobenzyl)-N-methylamino]ethyl}N-methylamino}acethydrazide (Compound 28)

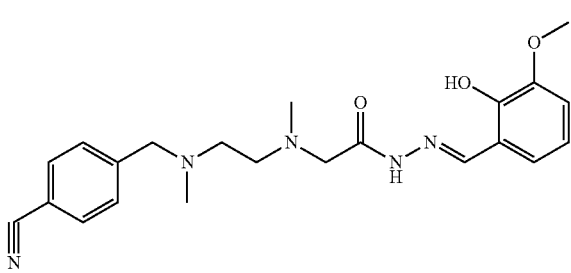 [SMILES: COc1cccc(/C=N/NC(=O)CN(C)CCN(C)Cc2ccc(C#N)cc2)c1O]

Intermediate 15 and o-vanilline were used as materials, and operations were the same for Example 1. Light yellow solid product was obtained. ¹H-NMR (400 MHz, CDCl3) δ: 11.31 (1H, s), 11.10 (1H, s), 8.36 (1H, s), 7.65 (4H, m), 6.92 (2H, m), 6.70 (1H, m), 3.94 (3H, s), 3.66 (2H, s), 3.27 (2H, s), 2.61 (4H, m), 2.31 (6H, m); EI-MS (m/z): 410.5[M+H]⁺.

Example 29: (E)-N'-(3-ethoxy-2-hydroxybenzal)-2-{N-{2-[N-(4-cyanobenzyl)-N-methylamino]ethyl}N-methylamino}acethydrazide (Compound 29)

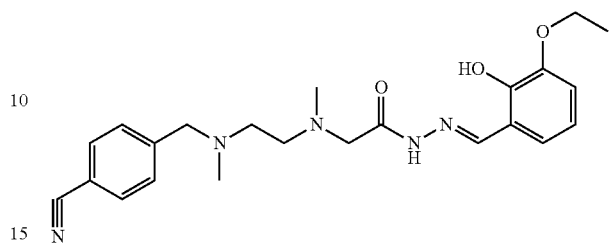

Intermediate 15 and 3-ethoxysalicylic aldehyde were used as raw materials, and operations were the same for Example 1. Light yellow solid product was obtained. ¹H-NMR (400 MHz, CDCl3) δ: 11.26 (1H, s), 10.90 (1H, s), 8.29 (1H, s), 7.63 (4H, m), 6.90 (3H, m), 4.14 (2H, m), 3.65 (2H, s), 3.25 (2H, s), 2.59 (4H, m), 2.29 (6H, m), 1.48 (3H, m); EI-MS (m/z): 424.4[M+H]⁺.

Example 30: (E)-N'-(4-N,N-diethylamino-2-hydroxybenzal)-2-{N-{2-[N-(4-cyanobenzyl)-N-methylamino]ethyl}N-methylamino}acethydrazide (Compound 30)

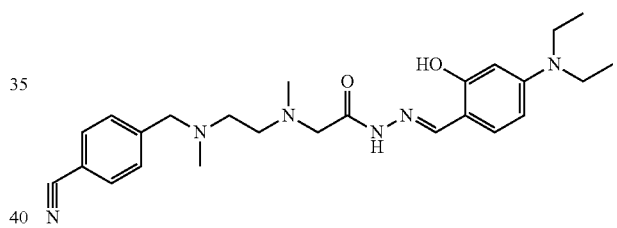

Intermediate 15 and 4-(diethylamino)salicylic aldehyde were used as raw materials, and operations were the same for Example 1. Light yellow solid product was obtained. ¹H-NMR (400 MHz, CDCl3) δ: 11.13 (1H, s), 10.85 (1H, s), 7.96 (1H, s), 7.64 (4H, m), 6.75 (1H, m), 6.20 (2H, m), 3.63 (2H, s), 3.37 (4H, pi), 3.23 (2H, s), 2.60 (4H, m), 2.33 (3H, s), 2.23 (3H, s), 1.19 (6H, in); ELMS (m/z): 451.5[M+H]⁺.

Example 31: (E)-N'-(3-methoxy-2-hydroxybenzal)-2-{N-{2-[N-(4-tert-butylbenzyl)-N-methylamino]ethyl}N-methylamino}acethydrazide (Compound 31)

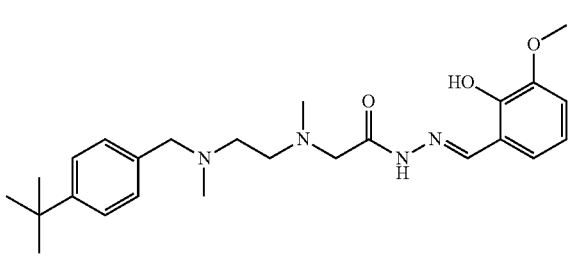 [SMILES: COc1cccc(/C=N/NC(=O)CN(C)CCN(C)Cc2ccc(C(C)(C)C)cc2)c1O]

Intermediate 18 and o-vanilline were used as raw materials, and operations were the same for Example 1. Light yellow solid product was obtained. $^1$H-NMR (400 MHz, CDCl3) δ: 11.92 (1H, s), 10.41 (1H, s), 7.72 (1H, s), 7.42 (4H, m), 6.90 (2H, m), 6.40 (1H, m), 3.90 (3H, s), 3.57 (2H, s), 3.29 (2H, s), 2.63 (4H, m), 2.40 (3H, s), 2.21 (3H, s), 1.32 (9H, m); EI-MS (m/z): 441.5[M+H]$^+$.

Example 32: (E)-N'-(3-ethoxy-2-hydroxybenzal)-2-{N-{2-[N-(4-tert-butylbenzyl)-N-methylamino]ethyl}N-methylamino}acethydrazide (Compound 32)

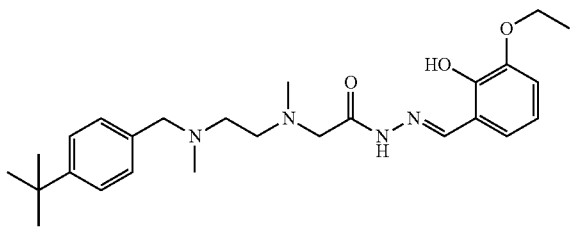 [SMILES: CCOc1cccc(/C=N/NC(=O)CN(C)CCN(C)Cc2ccc(C(C)(C)C)cc2)c1O]

Intermediate 18 and 3-ethoxysalicylic aldehyde were used as raw material, and operations were the same for Example 1. Light yellow solid product was obtained. $^1$H-NMR (400 MHz, CDCl3) δ: 11.86 (1H, s), 11.29 (1H, s), 7.69 (1H, m), 7.39 (4H, m), 6.87 (1H, m), 6.72 (1H, m), 6.38 (1H, m), 4.12 (2H, s), 3.56 (2H, s), 3.27 (2H, s), 2.61 (4H, m), 2.38 (3H, s), 2.18 (3H, s), 1.46 (3H, m) 1.32 (9H, m); ELMS (m/z): 455.5[M+H]$^+$.

Example 33: (E)-N'-(4-N,N-diethylamino-2-hydroxybenzal)-2-{N-{3-[N-(4-tert-butylbenzyl)-N-methylamino]propyl}N-methylamino}acethydrazide (Compound 33)

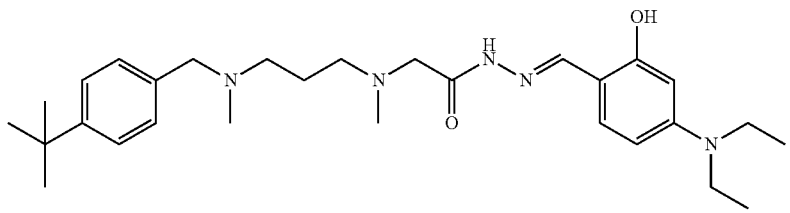 [SMILES: CCN(CC)c1ccc(/C=N/NC(=O)CN(C)CCCN(C)Cc2ccc(C(C)(C)C)cc2)c(O)c1]

Intermediate 21 and 4-(diethylamino)salicylic aldehyde were used as raw materials, and operations were the same for Example 1. Light yellow solid product was obtained. $^1$H-NMR (400 MHz, CDCl3) δ: 11.13 (1H, s), 10.19 (1H, s), 8.10 (1H, s), 7.29 (2H, m), 7.23 (2H, m), 6.87 (1H, m), 6.18 (2H, m), 3.48 (2H, s), 3.33 (4H, m), 3.16 (2H, s), 2.52 (2H, m), 2.45 (2H, m), 2.33 (3H, s), 2.22 (3H, s), 1.74 (2H, m), 1.27 (9H, s), 1.17 (6H, m); ELMS (m/z): 496.2[M+H]$^+$.

The compounds of the present invention were screened with EGFP-HIF-1α-CHOhIR cell model to show pharmacological activity of inhibiting proline hydroxylase and thereby stabilizing HIF-1α, which was illustrated as follows:

Experimental Example 1: Evaluation of Activity of the Compounds of the Present Invention in Stabilization of HIF-1α

The compounds were formulated with DMSO to form 30 mM stock solutions, and then formulated with analytical nutrient solution to form 2× working solutions, and seven final concentrations, 0.03, 0.1, 0.3, 1, 3, 10, 30 μM, were used for screening and obtaining dose-effect relationship. Positive compound bipyridine was formulated with DMSO to form 100 mM mother solution, and then formulated with analytical nutrient solution to form 2× working solution. The positive compound bipyridine in final concentration of 100 μM was used as control, and analytic nutrient solution with DMSO in a final concentration of 3‰ was used as solvent control.

CHOhIR cells (purchased from Thermo Fisher Scientific) which stably expressed EGFP-HIF-1α fusion protein were cultured under 37° C. and 5% $CO_2$ in F12 culture solution containing 0.5 mg/ml G418 and 10% FBS, transplanted in an amount of 0.8×10$^4$ cells/100 μl/well on a 96-well culture plate that could be subjected to fluorescence detection, and cultured under 37° C. and 5% $CO_2$ for 18-24 h. The cells were washed with analytical nutritional solution in amount of 100 μl/well, added with analytical nutritional solution in amount of 100 μl/well, added with 2× drug in amount of 100 μl/well, and each concentration was repeated in 3 wells in parallel way. After the cells were incubated under 37° C. and 5% $CO_2$ for 3 h, 12% formaldehyde in amount of 100 μl/well was added, fixation was carried out at room temperature for 30 min. Culture media was discarded, and the plate was washed with PBS twice, PBS containing 1 μM Hoechst was used, staining was performed at room temperature for 1 h. Detection was performed by IN Cell Analyzer 1000 live cell imaging system. Detection conditions were: 20× objective lens, excitation wavelength Ex=460 nm, emission wavelength Em=535 nm, exposure 300 ms to detect blue-fluorescence of cell nucleus passage; excitation wavelength Ex=475 nm, emission wavelength Em=535 nm, exposure 500 ms to detect green-fluorescence EGFP of cytoplasm passage, and pictures were taken continuously in 5 fields of view for each well. IN Cell Analyzer 1000 Multitarget Analysis Module of GE Company was used for analyzing aggregation of green-fluorescence of HIF-1α in cell nucleus, and BP100 μM treatment group was used as 100% activation of HIF-1α.

Activation rate (%)=(luminance of cell nucleus of drug treatment group−luminance of cell nucleus of solvent control treatment group)/(luminance of cell nucleus of agonist BP treatment group−luminance of cell nucleus of solvent control treatment group)×100%

Among 3 wells for parallel detection of each concentration point, average value of 15 fields of view was used for calculation of activation rate.

The results were shown in Table 2.

TABLE 2

Effects of some example compounds in stabilization of HIF-1α activity ($EC_{50}$)

| Example No. | $EC_{50}$ (μM) |
| --- | --- |
| 1 | 2.29 ± 0.27 |
| 2 | 17.8 ± 4.81 |
| 3 | 2.11 ± 0.85 |
| 4 | 0.83 ± 0.18 |
| 5 | 0.78 ± 0.14 |
| 8 | 5.23 ± 1.39 |
| 10 | 0.60 ± 0.18 |
| 11 | 0.17 ± 0.04 |
| 13 | 0.80 ± 0.19 |
| 14 | 1.02 ± 0.34 |
| 15 | 11.20 ± 2.87 |
| 17 | 0.56 ± 0.15 |
| 18 | 2.28 ± 0.67 |
| 22 | 2.77 ± 0.31 |
| 23 | 0.76 ± 0.15 |
| 24 | 0.82 ± 0.09 |
| 25 | 7.19 ± 1.27 |
| 26 | 0.98 ± 0.10 |
| 27 | 7.75 ± 1.33 |
| 28 | 8.42 ± 3.15 |
| 29 | 2.77 ± 0.39 |
| 30 | 0.53 ± 0.02 |
| 31 | 2.76 ± 0.78 |
| 32 | 1.86 ± 0.57 |
| 33 | 0.13 ± 0.02 |
| Bipyridine | 41.35 ± 1.60 |

The results showed that the compounds of the present invention could effectively prevent HIF-1α from being degraded, had effects of stabilizing HIF-1α activity, and their efficiencies were far greater than that of the positive control bipyridine.

The experimental method in this example was a well-known method for detecting degradation of HIF-1α with proline hydroxylase, and when a compound was confirmed to be able to stabilize HIF-1α, it must inhibit proline hydroxylase by chelating $Fe^{2+}$. Hence, the compounds of the present invention were also confirmed to have effects of inhibiting proline hydroxylase.

In addition, when all of HIF-1α, HIF-2α and HIF-3a depend on $Fe^{2+}$ catalysis in proline hydroxylase degradation (Hirsila M, Koivunen P, Gunzler V, Kivirikko K I, Myllyharju J. Characterization of the human prolyl 4-hydroxylases that modify the hypoxia-inducible factor. J. Biol. Chem. 278(33), 30772-30780 (2003).), it could be also determined that the compounds of the present invention had effects of stabilizing HIF-2α, HIF-3α, or preventing them from being degraded.

Although specific models for carrying out the invention were described in details, those skilled in the art would understand that these details can be modified and changed according to the teachings of disclosures, and all these changes fall into the protection scope of the present invention. The whole protection scope of the present invention is given by the appended claims and any equivalents thereof.

What is claimed is:

1. A method for inhibiting proline hydroxylase or stabilizing HIF-1 in vivo or in vitro, comprising a step of administering to a subject or a cell in need thereof an effective amount of the compound of Formula I or a pharmaceutically acceptable salt thereof;

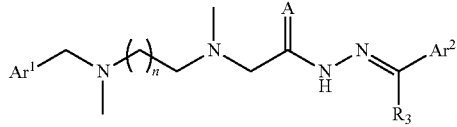

wherein:

n is 1, 2, 3, 4 or 5;

A is O or S;

$R_3$ is selected from hydrogen, and $C_1$-$C_4$ alkyl;

$Ar^1$ is an aryl substituted with $R_1$, wherein $R_1$ is selected from: hydrogen, $C_1$-$C_6$ alkyl, $C_1$-$C_6$ alkoxy, trifluoromethyl and cyano;

$Ar^2$ is an aryl substituted with $R_2$, $R_4$, and $R_5$, wherein $R_2$, $R_4$, and $R_5$ are independently selected from: hydrogen, hydroxy, $C_1$-$C_6$ alkyl, $C_1$-$C_6$ alkoxy, allyl, halogen and $C_1$-$C_4$ dialkylamino; wherein $R_2$, $R_4$ and $R_5$ are not hydrogen simultaneously.

2. The method according to claim 1, wherein the proline hydroxylase is prolyl-4-hydroxylase or EC 1.14.11.2.

3. The method according to claim 1, wherein the HIF-1 is HIF-α.

4. The method according to claim 3, wherein the HIF-α is HIF-1α, HIF-2α or HIF-3α.

5. The method according to claim 1, wherein the aryl is independently selected from phenyl, naphthyl, anthracenyl, phenanthrenyl, indenyl, fluorenyl and acenaphthenyl.

6. The method according to claim 1, wherein the $C_1$-$C_6$ alkyl is independently $C_1$-$C_4$ alkyl.

7. The method according to claim 1, wherein the $C_1$-$C_6$ alkoxy is independently $C_1$-$C_4$ alkoxy.

8. The method according to claim 1, wherein the $C_1$-$C_4$ dialkylamino is $C_1$-$C_3$ dialkylamino.

9. The method according to claim 1, wherein the halogen is selected from fluorine, chlorine, bromine and iodine.

10. The method according to claim 1, wherein:

n is 1 or 2;

A is O;

$R_3$ is hydrogen;

$Ar^1$ is phenyl or naphthyl substituted with $R_1$, wherein $R_1$ is selected from: hydrogen, $C_1$-$C_4$ alkyl, methoxy, ethoxy, trifluoromethyl, and cyano;

$Ar^2$ is phenyl or naphthyl substituted with $R_2$, $R_4$, and $R_5$, wherein $R_2$, $R_4$, and $R_5$ are independently selected from: hydrogen, hydroxy, $C_1$-$C_4$ alkyl, methoxy, ethoxy, allyl, halogen, dimethylamino, diethylamino and methylethylamino; wherein $R_2$, $R_4$, and $R_5$ cannot be hydrogen simultaneously.

11. The method according to claim 1, wherein the compound of Formula I is selected from:

(E)-N'-(3-methoxy-2-hydroxybenzal)-2-{N-{2-[N-(naphthalen-1-yl-methylene)-N-methylamino]ethyl}N-methylamino}acethydrazide, (E)-N'-(3,5-di-tert-butyl-2-hydroxybenzal)-2-{N-{2-[N-(naphthalen-1-yl-methylene)-N-methylamino]ethyl}N-methylamino}acethydrazide, (E)-N'-(3-ethoxy-2-hydroxybenzal)-2-{N-{2-[N-(naphthalen-1-yl-methylene)-N-methylamino]ethyl}N-methylamino}acethydrazide, (E)-N'-[(2-hydroxynaphthalen-1-yl)methylene]-2-{N-{2-[N-(naphthalen-1-yl-methylene)-N-methylamino]ethyl}N-methylamino}acethydrazide, (E)-N'-(4-N,N-diethylamino-2-hydroxybenzal)-2-{N-{2-[N-(naphthalen-1-yl-methylene)-N-methylamino]ethyl}N-methylamino}acethydrazide, (E)-N'-(3-bromo-4-hydroxybenzal)-2-{N-{2-[N-(naphthalen-1-yl-methylene)-N-methylamino]ethyl}N-methylamino}acethydrazide, (E)-N'-(4-bromobenzal)-2-{N-{2-[N-(naphthalen-1-yl-methylene)-N-methylamino]ethyl}N-methylamino}acethydrazide, (E)-N'-(3,5-di-tert-butyl-2-hydroxybenzal)-2-{N-{2-[N-(3-trifluoromethylbenzyl)-N-methylamino]ethyl}N-methylamino}acethydrazide, (E)-N'-(3-ethoxy-2-hydroxybenzal)-2-{N-{2-[N-(3-trifluoromethylbenzyl)-N-methylamino]ethyl}N-methylamino}acethydrazide, (E)-N'-(4-N,N-diethylamino-2-hydroxybenzal)-2-{N-{2-[N-(3-trifluoromethylbenzyl)-N-methylamino]ethyl}N-methylamino}acethydrazide, (E)-N'-(2,3-dihydroxybenzal)-2-{N-{2-[N-(3-trifluoromethylbenzyl)-N-methylamino]ethyl}N-methylamino}acethydrazide, (E)-N'-(3-methoxy-2-hydroxybenzal)-2-{N-{2-[N-(4-isopropylbenzyl)-N-methylamino]ethyl}N-methylamino}acethydrazide, (E)-N'-[(3-ethoxy-2-hydroxybenzal)methylene]-2-{N-{2-[N-(4-isopropylbenzyl)-N-methylamino]ethyl}N-methylamino}acethydrazide, (E)-N'-[(2-hydroxynaphthalen-1-yl)methylene]-2-{N-{2-[N-(4-isopropylbenzyl)-N-methylamino]ethyl}N-methylamino}acethydrazide, (E)-N'-(3,5-di-tert-butyl-2-hydroxybenzal)-2-{N-{2-[N-(4-isopropylbenzyl)-N-methylamino]ethyl}N-methylamino}acethydrazide, (E)-N'-(4-N,N-diethylamino-2-hydroxybenzal)-2-{N-{2-[N-(4-isopropylbenzyl)-N-methylamino]ethyl}N-methylamino}acethydrazide, (E)-N'-(2,3-dihydroxybenzal)-2-{N-{2-[N-(4-isopropylbenzyl)-N-methylamino]ethyl}N-methylamino}acethydrazide, (E)-N'-(3-bromo-6-hydroxybenzal)-2-{N-{2-[N-(4-isopropylbenzyl)-N-methylamino]ethyl}N-methylamino}acethydrazide, (E)-N'-(3-methoxy-2-hydroxybenzal)-2-{N-{2-[N-(3-methoxybenzyl)-N-methylamino]ethyl}N-methylamino}acethydrazide, (E)-N'-(3, 5-di-tert-butyl-2-hydroxybenzal)-3-(N-(2-(N-(4-tert-butylbenzyl)-N-methylamino)propyl)N-methyl-amino)acethydrazide, (E)-N'-[(2-hydroxynaphthalen-1-yl)methylene]-2-{N-{2-[N-(3-methoxybenzyl)-N-methylamino]ethyl}N-methylamino}acethydrazide, (E)-N'-(3,5-di-tert-butyl-2-hydroxybenzal)-2-{N-{2-[N-(3-methoxybenzyl)-N-methylamino]ethyl}N-methylamino}acethydrazide, (E)-N'-(4-N,N-diethylamino-2-hydroxybenzal)-2-{N-{2-[N-(3-methoxybenzyl)-N-methylamino]ethyl}N-methylamino}acethydrazide, (E)-N'-(2,3-dihydroxybenzal)-2-{N-{2-[N-(3-methoxybenzyl)-N-methylamino]ethyl}N-methylamino}acethydrazide, (E)-N'-(3-bromo-6-hydroxybenzal)-2-{N-{2-[N-(3-methoxybenzyl)-N-methylamino]ethyl}N-methylamino}acethydrazide, (E)-N'-[(2-hydroxynaphthalen-1-yl)methylene]-2-{N-{2-[N-(4-cyanobenzyl)-N-methylamino]ethyl}N-methylamino}acethydrazide, (E)-N'-(3,5-di-tert-butyl-2-hydroxybenzal)-2-{N-{2-[N-(4-cyanobenzyl)-N-methylamino]ethyl}N-methylamino}acethydrazide, (E)-N'-(3-methoxy-2-hydroxybenzal)-2-{N-{2-[N-(4-cyanobenzyl)-N-methylamino]ethyl}N-methylamino}acethydrazide, (E)-N'-(3-ethoxy-2-hydroxybenzal)-2-{N-{2-[N-(4-cyanobenzyl)-N-methylamino]ethyl}N-methylamino}acethydrazide, (E)-N'-(4-N,N-diethylamino-2-hydroxybenzal)-2-{N-{2-[N-(4-cyanobenzyl)-N-methylamino]ethyl}N-methylamino}acethydrazide, (E)-N'-(3-methoxy-2-hydroxybenzal)-2-{N-{2-[N-(4-tert-butylbenzyl)-N-methylamino]ethyl}N-methylamino}acethydrazide, (E)-N'-(3-ethoxy-2-hydroxybenzal)-2-{N-{2-[N-(4-tert-butylbenzyl)-N-methylamino]ethyl}N-methylamino}acethydrazide, and (E)-N'-(4-N,N-diethylamino-2-hydroxybenzal)-2-{N-{3-[N-(4-tert-butylbenzyl)-N-methylamino]propyl}N-methylamino}acethydrazide.

* * * * *